US012674206B2

(12) United States Patent
Arora et al.

(10) Patent No.: US 12,674,206 B2
(45) Date of Patent: *Jul. 7, 2026

(54) SYSTEMS AND METHODS FOR TREATING PATIENTS HAVING A GENETIC PREDISPOSITION TO DEVELOP PROSTATE CANCER

(71) Applicant: Institute For Cancer Research, Philadelphia, PA (US)

(72) Inventors: Sanjeevani Arora, Philadelphia, PA (US); Greg Enders, Philadelphia, PA (US); Erica Golemis, Philadelphia, PA (US); Emmanuelle Nicolas, Philadelphia, PA (US); Ilya Serebriiskii, Philadelphia, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 832 days.

This patent is subject to a terminal disclaimer.

(21) Appl. No.: 16/902,552

(22) Filed: Jun. 16, 2020

(65) Prior Publication Data

US 2021/0010087 A1 Jan. 14, 2021

Related U.S. Application Data

(63) Continuation of application No. 14/855,999, filed on Sep. 16, 2015, now Pat. No. 10,724,100.

(51) Int. Cl.
*C12Q 1/6886* (2018.01)
*G01N 33/57555* (2026.01)

(52) U.S. Cl.
CPC ..... *C12Q 1/6886* (2013.01); *G01N 33/57555* (2026.01); *C12Q 2600/118* (2013.01); *C12Q 2600/156* (2013.01); *G01N 2800/52* (2013.01)

(58) Field of Classification Search
CPC ............ C12Q 1/6886; C12Q 2600/106; C12Q 2600/118; C12Q 2600/156; C12Q 2600/158; G01N 33/57434; G01N 2800/52
See application file for complete search history.

(56) References Cited

U.S. PATENT DOCUMENTS

| | | | | |
|---|---|---|---|---|
| 10,724,100 | B2 * | 7/2020 | Arora ................... | C12Q 1/6886 |
| 2008/0253632 | A1 | 10/2008 | Halazonetis | |
| 2010/0324112 | A1 | 12/2010 | Gollin et al. | |
| 2012/0021935 | A1 | 1/2012 | Cazaux et al. | |
| 2012/0220645 | A1 | 8/2012 | Gollin et al. | |

FOREIGN PATENT DOCUMENTS

| | | |
|---|---|---|
| EP | 2784165 | 10/2014 |
| WO | 2008129239 | 10/2008 |
| WO | 2012109500 | 8/2012 |
| WO | 2014047092 | 3/2014 |

OTHER PUBLICATIONS

Van Oorschot, B. et al. International Journal of Radiation Oncology Biology Physics 88(3):664-670 (Mar. 2014). (Year: 2014).*
Olive, P.L. et al. Radiotherapy and Oncology 86:336-346. (Year: 2008).*
Pugh, T.J. et al. Clinical Cancer Research 15(15):5008-5016. (Year: 2009).*
Ismail et al., "An optimized method for detecting gamma-H2AX in blood cells reveals a significant interindividual variation in the gamma-H2AX response among humans", Nucleic Acids Research, 2007, 35(5), pp. 1-10.
Hegele, "SNP Judgments and Freedom of Association", Arterioscler Thromb Vasc Biol, 2002, 22, p. 1058-1061.
Lucentini, "Gene Association Studies Typically Wrong", The Scientist, 2004, 18(24), pp. 1-6.
Scarpato et al., "Nuclear damage in peripheral lymphocytes of obese and overweight Italian children as evaluated by the gamma-H2AX focus assay and micronucleus test", The FASEB Journal, 2017, 25(2), pp. 685-693.
Lockett et al., "DNA Damage Levels in Prostate Cancer Cases and Controls", Carcinogenesis, 2005, 27(6), pp. 1187-1193.
Kuo et al., "Gamma-H2AX—A Novel Biomarker for DNA Double-Strand Breaks", In Vivo, 2008, 22, pp. 305-310.
Nicolas et al., "Systematic Evaluation of Underlying Defects in DNA Repair as an Approach to Case-Only Assessment of Familial Prostate Cancer", Oncotarget, 2015, pp. 39614.
Brzozowska et al., "In vivo versus In vitro Individual radiosensitivity analyzed in healthy donors and in prostate cancer patients with and without severe side effects after radiotherapy", International Journal of Radiation Biology, 2012, 88(5), pp. 405-413.
International Search Report and Written Opinion issued in PCT/US2016/052036 dated Jan. 5, 2017.
Polkinghorn et al., "Androgen Receptor Signaling Regulates DNA Repair in Prostate Cancers", Cancer Discovery, 2013, pp. 1245-1253.
Sun et al., "The Impact of Common Genetic Variations in Genes of the Sex Hormone Metabolic Pathways on Steroid Hormone Levels and Prostate Cancer Aggressiveness", Cancer Prev Res, 2011, 4(12), pp. 2044-2050.

(Continued)

*Primary Examiner* — Diana B Johannsen
(74) *Attorney, Agent, or Firm* — Duane Morris LLP

(57) ABSTRACT

Systems and methods for mitigating prostate cancer development are provided. Peripheral blood cells may be evaluated for the presence or quantity of gamma-H2AX foci, and/or for gene alterations encoding a protein with impaired or lack of function, for example, because the encoded protein is truncated, and correlating with prostate cancer development. Such nucleic acids may encode proteins from or peripheral to the DNA damage repair pathway and/or androgen receptor signaling pathway, or that are otherwise correlated with prostate cancer development. Such genes include one or more of AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, or NOTCH2.

22 Claims, 7 Drawing Sheets

Specification includes a Sequence Listing.

(56) References Cited

OTHER PUBLICATIONS

Wood et al., "Human DNA Repair Genes", Science, 2001, 291, pp. 1284-1289.

Agesen et al., "ColoGuideEx: a robust gene classifier specific for stage II colorectal cancer prognosis", Gut Epub 02, 2010, 61(11), pp. 1560-1567.

Cai et al., "Computational analysis of the No., area and density of gamma-H2AX foci in breast cancer cells exposed to (111)In-DTPA-hEGF or gamma-rays using Image-J software", Int J Radiat Biol, 2009, 85(3), pp. 262-271.

Cattaneo et al., "Pathways and Crossroads to Colorectal Cancer", Pre-Invasive Disease: Pathogenesis and Clinical Management, 2011, pp. 369-394.

Cimino et al., "Aneuploidy in mammalian somatic cells in vivo", Mutation Research, 1986, 167, pp. 107-122.

GenBank Accession No. BC_117141, 3 pages (Sep. 2006).

GenBank Accession No. NM_000124, 8 pages (Sep. 2013).

GenBank Accession No. NM_198253, 7 pages (Oct. 2013).

International Search Report and Written Opinion dated Feb. 21, 2014 issued in PCT/US13/60264.

Ivashkevich et al., "gammaH2AX foci as a measure of DNA damage: a computational approach to automatic analysis", Mutat Res, 2011, 711(1-2), pp. 49-60.

Kennedy et al., "Development and independent validation of a prognostic assay for stage II colon cancer using formalin-fixed paraffin-embedded tissue", J Clin Oncol, 2011, 29(35), pp. 4620-4626.

Kucherlapati et al., "Comprehensive Molecular Characterization of Human Colon and Rectal Cancer", Nature, 2012, 487(7407), pp. 330-337.

Muslimovic et al., "Measurement of H2AX Phosphorylation as a Marker of Ionizing Induced Cell Damage", 2012, pp. 3-21.

Non-final Office Action mailed Nov. 4, 2014 in related U.S. Appl. No. 13/833,946.

Novotna et al., "Role of [gamma]-H2AX in DNA-Damage Response and its Possible Clinical Applications", Mil Med Sci Lett, 2011, 80(4), pp. 169-177.

Oka et al., "DNA damage signaling is activated during cancer progression in human colorectal carcinoma", Cancer Biol Ther, 2010, 9(3), pp. 246-252.

Redon et al., "Histone gammaH2AX and poly(ADP-ribose) as clinical pharmacodynamic biomarkers", Clin Cancer Res, 2010, 16(18), pp. 4532-4542.

Risques et al., "Ulcerative colitis is a disease of accelerated colon aging: evidence from telomere attrition and DNA damage", Gastroenterology, 2008, 135(2), pp. 410-418.

Runge et al., "Fully automated interpretation of ionizing radiation-induced [gamma]H2AX foci by the novel pattern recognition system AKLIDES", Int J Radiat Biol, 2012, 88(5), pp. 439-447.

Salazar et al., "Gene expression signature to improve prognosis prediction of stage II and III colorectal cancer", J Clin Oncol, 2011, 29, pp. 17-24.

Sedelnikova et al., "y-H2AX in Cancer Cells: A potential biomarker for cancer diagnostics, prediction and recurrence", Cell Cycle, 2006, 5(24), pp. 2909-2913.

Takabayashi et al., "Alteration of the DNA damage response in colorectal tumor progression", Human Pathology, 2013, 44(6), pp. 1038-1046.

Tan et al., "Genetics: an 18-gene signature (ColoPrint) for colon cancer prognosis", Nat Rev Clin Oncol, 2011, 8, pp. 131-133.

Venook et al., "Is there currently an established role for the use of predictive or prognostic molecular markers in the management of colorectal cancer? A point/counterpoint", 2010, pp. 193-200.

Wood et al., "The Genomic Landscape of Human Breast and Colorectal Cancers", Science, 2007. 318, pp. 1108-1113.

Zlobinskaya et al., "Induction and repair of DNA double-strand breaks assessed by y-H2AX foci after irradiation with pulsed or continuous proton beams", Radiat Environ Biophys, 2012, 51(1), pp. 23-32.

Tischkowitz et al., "Analysis of the Gene Coding for the BRCA2-Interacting Protein PALB2 in Hereditary Prostate Cancer", The Prostate, 2008, 68, pp. 675-678.

* cited by examiner

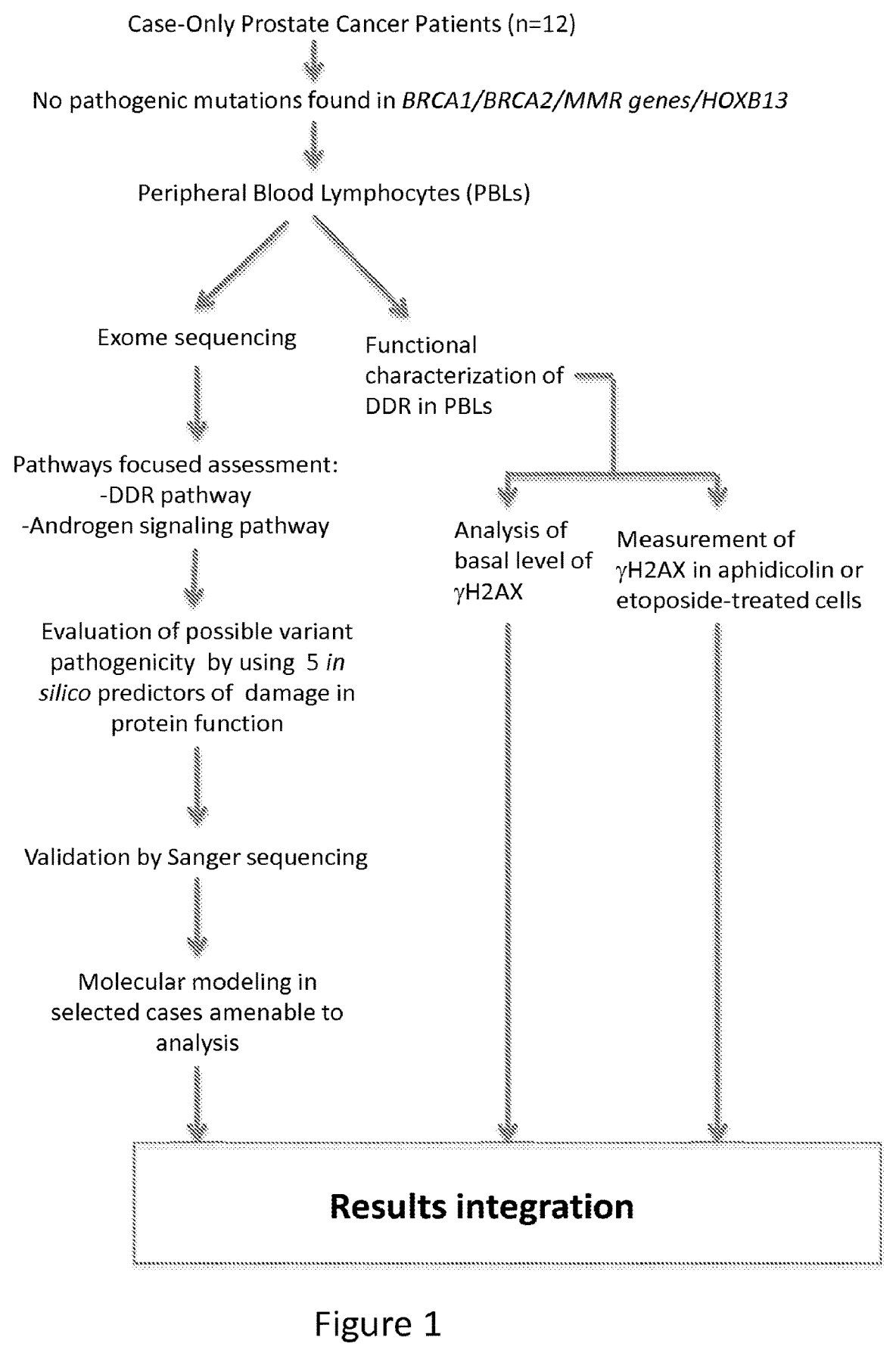

Case-Only Prostate Cancer Patients (n=12)

No pathogenic mutations found in *BRCA1/BRCA2/MMR genes/HOXB13*

Peripheral Blood Lymphocytes (PBLs)

Exome sequencing

Functional characterization of DDR in PBLs

Pathways focused assessment:
-DDR pathway
-Androgen signaling pathway

Analysis of basal level of γH2AX

Measurement of γH2AX in aphidicolin or etoposide-treated cells

Evaluation of possible variant pathogenicity by using 5 *in silico* predictors of damage in protein function Validation by Sanger sequencing Molecular modeling in selected cases amenable to analysis

Results integration

Figure 1

AKR1C1

PAPSS2

Area under ROC curve = 0.8778

SYSTEMS AND METHODS FOR TREATING PATIENTS HAVING A GENETIC PREDISPOSITION TO DEVELOP PROSTATE CANCER

REFERENCE TO GOVERNMENT GRANTS

This invention was made with government support under P30 CA006927 awarded by the National Institutes of Health. The government has certain rights in the invention.

REFERENCE TO A SEQUENCE LISTING

This application includes a Sequence Listing submitted electronically as a text file named Prostate_Cancer_Gene_ST25.txt, created on Sep. 14, 2015 with a size of 180,000 bytes. The Sequence Listing is incorporated by reference herein.

FIELD OF THE INVENTION

The invention relates generally to the field of cancer treatment. More particularly, the invention relates to methods for diagnosing a genetic predisposition to develop prostate cancer, then treating to inhibit development of prostate cancer.

BACKGROUND OF THE INVENTION

Various publications, including patents, published applications, accession numbers, technical articles and scholarly articles are cited throughout the specification. Each of these cited publications is incorporated by reference, in its entirety and for all purposes, in this document.

Prostate cancer is the most common noncutaneous cancer and the second-leading cause of cancer-related death in men in the United States. Prior studies have shown that family history, such as a brother or father with prostate cancer and relatives affected at an early age, is a major risk factor. A growing consensus in the field is that inherited factors for prostate cancer are highly heterogeneous, involving mutations in high penetrance genes that occur in a small number of families, but also alterations in low or moderate penetrance genes that are more common, and which may interact in individuals to promote disease. While a few genes such as BRCA2 and HOXB13 are definitively linked to prostate cancer risk in small patient populations, a greater proportion of prostate cancer risk may be associated with low incidence alleles of intermediate penetrance. While panel testing may be useful in detecting some of these variants, it is difficult to design a panel that adequately captures the rapidly increasingly number of rare variants associated with multiple forms of cancer. With the cost of DNA sequencing rapidly decreasing, analysis of exome and genome data is becoming an alternative approach. However, given the computational complexity of assessing the many rare variants found in every individual, particularly if multiple independent variants may be interacting to produce risk, it is desirable to employ a robust analytic pathway grounded in understanding of the physiological basis of the disease.

In addition to genetic heterogeneity of prostate cancer susceptibility, another common scenario in clinical cancer risk evaluation that impacts the assessment of genetic variants is a "case-only" presentation for genetic testing. This may arise when a patient presents for cancer risk evaluation with small family structure, limited family history information, and limited access to specimens from other affected relatives due to death or other causes. In this situation, the ability to clarify cancer susceptibility of genetic variants using family history or by testing a DNA sample from one or more informative blood relatives (affected or unaffected with cancer) is not possible. Such pedigrees will often be characterized by some prostate cancers, but also other cancers, raising the possibility that some inherited variants may be risk factors for multiple cancer types. In the clinical cancer risk assessment setting, novel pathway-based approaches to identifying at-risk individuals and families are greatly needed.

SUMMARY OF THE INVENTION

Provided herein are methods for reducing the risk of developing prostate cancer in subjects. The methods screen cells obtained from the subject for at least the presence of germline nucleic sequence alterations in select genes that have been associated with a predisposition to develop prostate cancer. The alterations may encode truncated proteins, or may encode functionally-impaired proteins, or may encode proteins that lack functionality relative to the unaltered form of the protein. The genes may encode a protein from one or more of a DNA damage repair pathway, an androgen receptor signaling pathway, a protein that is peripheral to a DNA damage repair pathway or an androgen receptor signaling pathway, or that is otherwise associated with prostate cancer development or a prostate cancer predisposition risk, for example, when the gene encoding the protein is altered.

In some aspects, the methods further comprise screening the cells for the presence of genomic instability, double stranded DNA breaks, and/or elevated levels of gamma-H2AX foci. Prior to this screen, the cells may be treated with an agent or with radiation, preferably at a low dose, in order to induce double stranded DNA breaks or to induce the double stranded break DNA repair system in the cells.

Based on the determination of the presence of one or more alterations in the one or more genes, it may be determined whether the subject has prostate cancer or whether the subject has a predisposition to develop prostate cancer. Or, based on the determination of the presence of one or more alterations in the one or more genes and on the determination of the presence of one or more of double stranded DNA breaks, genomic instability, or elevated gamma-H2AX foci, it may be determined whether the subject has prostate cancer or whether the subject has a predisposition to develop prostate cancer. If it is determined that the subject has prostate cancer, or that the subject has a predisposition to develop prostate cancer, then the subject is treated with a treatment regimen that prevents or inhibits the development of prostate cancer, or that prevents or inhibits the progression of prostate cancer. Such a treatment regimen may include one or more of a prostatectomy, DNA-damaging therapy, androgen deprivation therapy, chemotherapy, chemopreventive therapy, nutritional supplementation, and/or enhanced monitoring.

The alterations in the genes may comprise rare variants, non-rare variants, or a combination thereof. The rare variants may comprise rare single nucleotide variants.

The methods may screen any of the genes from Table 3 or Table 4 herein for the presence of alterations. The methods may screen one or more of the following genes for the presence of alterations: aldo-keto reductase family 1, member C1 (AKR1C1), partner and localizer of BRCA2 (PALB2), ataxin (APTX), bloom syndrome protein (BLM), breast cancer 1 (BRCA1), C-terminal binding protein 1 (CTBP1), damage-specific DNA binding protein 2 (DDB2), Fanconi Anemia complementation group A (FANCA), Fanconi Anemia complementation group L (FANCL), methyl-CpG-binding domain protein 5 (MBD5), mutS homolog 3 (MSH3), nei-like DNA glycosylase 3 (NEIL3), RAD51 paralog D (RAD51D), helicase ARIP4/androgen receptor-interacting protein 4 (RAD54L2), Sp1 transcription factor (SP1), tumor suppressor p53 binding protein 1 (TP53BP1), ubiquitin-conjugating enzyme E2 D3 (UBE2D3), ubiquitin-conjugating enzyme E2 V2 (UBE2V2), 3'-phosphoadenosine 5'-phosphosulfate synthase 2 (PAPSS2), ATPase, H+ transporting, lysosomal, V0 subunit A2 (ATP6VOA2), UDP-N-acetylglucosamine transferase subunit (ALG13), mannosyl (alpha-1,6-)-glycoprotein beta-1,2-N-acetylglucosaminyltransferase (MGAT2), beta-1,3-glucuronyltransferase 3 (B3GAT3), dolichol kinase (DOLK), fms-like tyrosine kinase 3 (FLT3), additional sex combs like transcriptional regulator 1 (ASXL1), kinase insert domain receptor (KDR), Notch 2 (NOTCH2), nuclear receptor interacting protein 1 (NRIP1), EF-hand calcium binding domain 6 (EFCAB6), and/or cysteine-rich secretory protein 3 (CRISP3). The genes may be screened for the presence of one or more alterations in one or more of these genes. Any combination of one or more of these genes may be included in the screen.

BRIEF DESCRIPTION OF THE DRAWINGS

FIG. 1 shows the study operational logic. After review of family history and negative results for genetic testing for known predisposing factors, 12 DNA samples isolated from peripheral blood lymphocytes (PBLs) of 12 patients with prostate cancer were sent for exome sequencing. Data analysis included identification of the rare variants in 826 genes selected as described in Table 2 and validation by Sanger sequencing of the variants that scored non neutral by at least 3 in silico predictors. Two variants (in AKR1C1 and PAPSS2) were further characterized by molecular modeling. PBLs were also used to assess the response to DNA damaging agents.

FIG. 2A shows a radar plot indicating percent of genes that are AR-associated, induced by androgens or direct AR targets in each class of DNA repair genes. Classes of DDR genes are based on Table 2, except that the two classes "Base excision repair (BER)" and "Other BER and strand break joining factors" were merged. Vertical black numbering indicates percent of AR-associated genes; numbering around the perimeter indicates the number of genes in each class. FIG. 2B. shows a simplified representation of DNA interstrand crosslink damage being repaired by proteins in Fanconi's anemia pathway. Variants found in patient 124604 include FANCA, BLM, and PALB2; those found in patient 117939 include MSH3 and FANCL. FIG. 2C shows alternative binding by TP53BP1 or BRCA1 specifies NHEJ versus HR DNA repair, with variants in each gene found in patient 129413.

FIG. 3A shows AKR1C1, S221N. AKR1C1 catalyzes the inactivation of progesterone to the less potent 20α-hydroxyl-pregn-4-ene-3-one. The reaction is NADPH dependent with an obligatory requirement for the cofactor to bind before the steroid substrate can bind to form the central complex. The progesterone is maintained in a steroid binding site at H222; an H222I mutation decreases the Km value for NADPH 95-fold. Here, AKR1C1 (PDB code: 1MRQ) is shown with bound steroid 20alpha-hydroxy-progesterone, and the cofactor, NADP+ in ball-and-stick representation. S221 and adjacent catalytic residue H222 of AKR1C1 are also shown. S221 is involved in 2 hydrogen bonds with adjacent residues and one with the NADP+ cofactor. Though predicted to be benign by several conservation based servers, the S221N substitution disrupts the hydrogen-bonding network required to maintain the catalytic active site configuration. FIG. 3B shows the PAPSS2 kinase domain, PUA (PseudoUridine synthase and Archaeosine transglycosylase) domain and sulfate adenylyltransferase domain. The position of the P454L and G270D missense variants are indicated.

FIG. 4A shows the mean number of γH2AX foci in vehicle treated patients and matched controls (p=0.746, not significant). FIG. 4B shows the mean number γH2AX foci per cell are depicted for cases and controls following drug treatment. Cases: 'x's, controls: triangles. Dashed lines: statistically optimal cutoff points to discriminate between samples with high and low γH2AX levels for each treatment or the two tests combined, as indicated. Using the combination (solid black line), 7/9 patients exhibited high γH2AX levels versus 1/10 controls. FIG. 4C shows an area under the receiver operating characteristic (ROC) curve (AUC) for the combined γH2AX scores for aphidicolin and etoposide demonstrates assays discriminate between patients and controls, AUC=0.8778.

DETAILED DESCRIPTION OF THE INVENTION

Figure 2A:
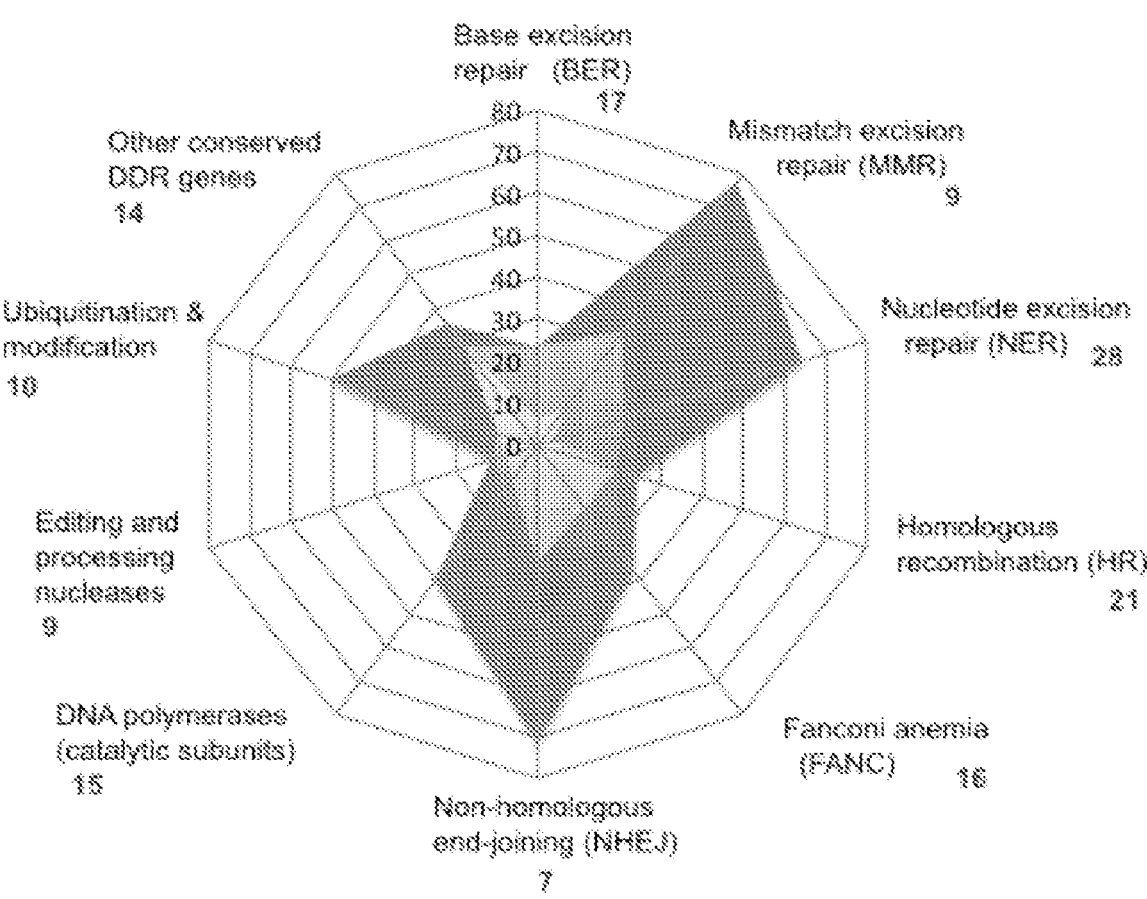
FIGS. 2A-2C show DNA damage response genes in prostate cancer patients

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

A molecule such as a polynucleotide has been "isolated" if it has been removed from its natural environment and/or altered by the hand of a human being.

A nucleotide in a nucleic acid sequence such as but not limited to a cDNA, mRNA, or derivative thereof may correspond to a nucleotide in the genomic nucleic acid sequence. In this respect, corresponding to comprises a positional relationship of nucleotides in the genomic DNA gene sequence relative to nucleotides in a polynucleotide sequence (e.g., cDNA, mRNA) obtainable from the genomic DNA sequence.

The terms subject and patient are used interchangeably. A subject may be any animal, and preferably is a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). Human beings are highly preferred.

It has been observed in accordance with the invention that alterations in genes encoding proteins involved in the DNA damage response, which alterations encode a functionally-impair protein, are predictive as to whether a patient may develop prostate cancer, and that these alterations may be detected in peripheral blood cells (e.g., lymphocytes). It was observed through germline exome data from individuals with prostate cancer and a family history of one or more cancer types that such alterations fall into two classes. The first class includes variants in genes associated with defects in the DNA damage response (DDR) pathway, indicating that genes such as BRIP1, MSH2, MSH3, CHEK2, and PALB2, have general function in contributing to early genomic instability in cancer. Of particular relevance to prostate cancer, the androgen receptor has been found to regulate a suite of DDR genes, including some that promote resistance to radiotherapy in prostate cancer in part by promotion of non-homologous end joining (NHEJ) repair. The second class includes variants in genes associated with the pathogenesis of non-familial prostate cancer, including those that regulate androgen signaling by various mechanisms. This disclosure identifies gene variants that predispose to prostate cancer development, with a particular bias toward DDR-impairing defects.

The alterations include missense, frameshift, stop gain, deletions, substitutions, insertions, rearrangements, start codon change, and combinations thereof, in the nucleic acid sequence of one or more of the genes listed in Table 3 and Table 4 below, or otherwise described or exemplified herein. It is believed that particular alterations are not critical, but instead, the predisposition arises from the existence of alterations in the genes identified through this disclosure. The alterations preferably encode a protein, that when expressed, has impaired functionality relative to the unaltered form, or has substantially no functionality relative to the unaltered form. The alterations may encode a truncated protein. Accordingly, any alteration in the genes from Table 3, Table 4, or otherwise described or exemplified herein, that encodes a functionally impaired, truncated, and/or nonfunctional protein may predispose to prostate cancer development.

Preferred gene variants that predispose to prostate cancer development include one or more alterations in one or more of aldo-keto reductase family 1, member C1 (AKR1C1), partner and localizer of BRCA2 (PALB2), aprataxin (APTX), bloom syndrome protein (BLM), breast cancer 1 (BRCA1), C-terminal binding protein 1 (CTBP1), damage-specific DNA binding protein 2 (DDB2), Fanconi Anemia complementation group A (FANCA), Fanconi Anemia complementation group L (FANCL), methyl-CpG-binding domain protein 5 (MBD5), mutS homolog 3 (MSH3), nei-like DNA glycosylase 3 (NEIL3), RAD51 paralog D (RAD51D), helicase ARIP4/androgen receptor-interacting protein 4 (RAD54L2), Sp1 transcription factor (SP1), tumor suppressor p53 binding protein 1 (TP53BP1), ubiquitin-conjugating enzyme E2 D3 (UBE2D3), ubiquitin-conjugating enzyme E2 V2 (UBE2V2), nuclear receptor interacting protein 1 (NRIP1), EF-hand calcium binding domain 6 (EFCAB6), cysteine-rich secretory protein 3 (CRISP3), 3'-phosphoadenosine 5'-phosphosulfate synthase 2 (PAPSS2), ATPase, H+ transporting, lysosomal, V0 subunit A2 (ATP6V0A2), UDP-N-acetylglucosamine transferase subunit (ALG13), mannosyl (alpha-1,6-)-glycoprotein beta-1,2-N-acetylglucosaminyltransferase (MGAT2), beta-1,3-glucuronyltransferase 3 (B3GAT3), dolichol kinase (DOLK), fms-like tyrosine kinase 3 (FLT3), additional sex combs like transcriptional regulator 1 (ASXL1), kinase insert domain receptor (KDR), or Notch 2 (NOTCH2). In a patient, any combination of these genes having alterations may predispose to prostate cancer development.

In addition to gene alterations, it is believed that patients predisposed to prostate cancer development also exhibit genomic instability, double stranded DNA breaks, and/or enhanced gamma-H2AX foci. Thus, the combination of genomic instability, double stranded DNA breaks, and/or enhanced gamma-H2AX foci with one or more of the altered genes described or exemplified herein may serve as a marker for a predisposition to develop prostate cancer. The one or more altered genes may serve as a marker for a predisposition to develop prostate cancer by themselves, for example, in the absence of a combination with genomic instability, double stranded DNA breaks, and/or enhanced gamma-H2AX foci. Accordingly, the invention features methods for determining whether a patient has a predisposition to develop prostate cancer and, if so, treating the patient in a way that inhibits or prevents prostate cancer development. The methods are preferably carried out in vivo.

The screen for genomic instability, double stranded DNA breaks, and/or enhanced gamma-H2AX foci and/or the one or more of the altered genes is preferably carried out using nuclear material and nucleic acids obtained/isolated from peripheral blood lymphocytes. Thus, in some aspects, the methods comprise obtaining peripheral blood lymphocytes from a subject.

In aspects where the screening method includes assessment of genomic instability, double stranded DNA breaks, and/or enhanced gamma-H2AX foci, the genomic instability and/or double stranded DNA breaks may be determined from nucleic acids from the peripheral blood lymphocytes, and gamma-H2AX foci may be determined from the lymphocytes or nucleus thereof. Determining genomic instability, double stranded DNA breaks, and/or gamma-H2AX foci may be carried out according to any suitable method, including the methods described or exemplified herein. The determined genomic instability, double stranded DNA breaks, and/or gamma-H2AX foci may be compared with quantitative or qualitative reference values for genomic instability, double stranded DNA breaks, and/or gamma-H2AX foci associated with a predisposition to develop prostate cancer, and optionally with quantitative or qualitative reference values for genomic instability, double stranded DNA breaks, and/or gamma-H2AX foci not associated with a predisposition to develop prostate cancer, for example, reference values of a healthy subject or a subject not at risk to develop prostate cancer based on these markers. The reference values may, for example, comprise values indicative of a high risk for developing prostate cancer, values indicative of a moderate risk for developing prostate cancer, and/or values indicative of a low risk for developing prostate cancer. The comparing step may be carried out using a processor programmed to compare determined quantitative or qualitative values for genomic instability, double stranded DNA breaks, and/or gamma-H2AX foci with quantitative or qualitative reference values for such markers.

In some preferred aspects, the peripheral blood lymphocytes are contacted with a DNA damaging agent, or with DNA damaging radiation prior to screening for genomic instability, double stranded DNA breaks, and/or gamma-H2AX foci. The DNA damaging agent may induce double stranded breaks in DNA. The DNA damaging agent may include any agent that activates the double stranded DNA break repair system in a cell. The DNA damaging agent may comprise aphidicolin or etoposide. The radiation may comprise ultraviolet radiation or ionizing radiation. In highly preferred aspects, the DNA damaging agent is contacted with the lymphocytes at a low dose or sub-optimal dose. A low dose may include an amount of the agent or radiation that is lower than the manufacturer's recommended amount for a DNA damage assay. A low dose enhances the double stranded breaks and gamma-H2AX foci sufficient to give the screen higher confidence, but does not produce an excessive amount of background noise/DNA breaks.

Gamma-H2AX foci may be determined, for example, using immunoblotting, immunofluorescence, immunohisto-chemistry, ELISA, flow cytometry, or other methodology that includes, for example, a detectably-labeled antibody that specifically binds to gamma-H2AX foci. The foci may be assessed in permeabilized peripheral blood lymphocytes. Detection of the detectably-labeled antibody may thus visualize the foci, and may serve as the basis for quantification. Genomic instability may be determined, for example, from a metaphase spread or a karyotype obtained from the lymphocytes.

The methods preferably include assessment of alterations in one or more genes that predispose a subject to develop prostate cancer. The alterations preferably occur in germline nucleic acid sequences. Thus, the methods preferably comprise identifying one or more germline nucleic acid sequence alterations in one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes, or any other genes listed in Table 3 or Table 4.

Without intending to be limiting to particular sub-categories or categories, the genes may be sub-categorized in some aspects. For example, the one or more genes may encode a protein from a DNA damage repair pathway, an androgen receptor signaling pathway, or both a DNA damage repair and an androgen receptor signaling pathway, such as one or more of AKR1C1, PALB2, APTX, BLM, BRCA1, CCTBP1, DDB2, FANCA, FANCL, MBD5, MSH3, NEIL3, RAD51D, RAD54L2, SP1, TP53BP1, UBE2D3, and/or UBE2V2. The one or more genes may encode a protein that is peripheral to a DNA damage repair pathway or androgen receptor signaling pathway, such as one or more or NRIP1, EFCAB6, and/or CRISP3. The one or more genes may encode a protein that is otherwise associated with prostate cancer disposition, which proteins may or may not be part of or peripheral to a DNA damage repair pathway, an androgen receptor signaling pathway, or both a DNA damage repair and an androgen receptor signaling pathway, such as one or more of PAPSS2, ATP6V0A2, ALG13, MGAT2, B3GAT3, DOLK, FLT3, ASXL1, KDR, and/or NOTCH2.

In some detailed aspects, the methods comprise comparing nucleic acid sequences. For example, such methods may comprise the steps of comparing the sequence of a nucleic acid comprising the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, RAD54L2, BRCA1, EFCAB6, CRISP3, PAPSS2, ATP6V0A2, ALG13, MGAT2, B3GAT3, DOLK, FLT3, ASXL1, KDR, and/or NOTCH2 gene obtained from a subject with one or more reference nucleic acid sequences comprising one or more alterations in the respective AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 gene sequences, which alterations predispose a subject to develop prostate cancer (e.g., because they encode a protein with impaired function or substantially no function), or with one or more reference nucleic acid sequences comprising no alteration in the respective AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 gene sequences, or comprising one or more alterations that is not associated with prostate cancer development. The reference nucleic acid sequences serve as a standard against which the subject-obtained sequences may be compared in order to determine whether the subject-obtained sequences include alterations that predispose the subject to develop prostate cancer. The alterations being screened-for preferably encode the respective protein that has an impaired function or substantially no function relative to the unaltered form. From the comparison of subject-obtained gene sequences and reference sequences, it may be determined if the patient has one or more alterations encoding a protein that has an impaired function or substantially no function relative to the unaltered form or that otherwise predisposes to prostate cancer development. The reference nucleic acid sequences may thus be based on alterations that predispose to develop prostate cancer, and/or based on control sequences that do not have alterations that predispose to develop prostate cancer.

The alterations may comprise rare variants, non-rare variants, or any combination of rare and non-rare variants. The rare variants may comprise rare single nucleotide variants.

The comparing step may be carried out using a processor programmed to compare nucleic acid sequences, for example, to compare the nucleic acid sequences obtained from the subject and the reference nucleic acid sequences. The methods may optionally include the step of determining the sequence of the nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 gene. The methods may comprise the step of diagnosing whether the subject has a predisposition to genomic instability and/or has a predisposition to develop prostate cancer based on the presence or absence of an alteration associated with a predisposition to genomic instability and/or to develop prostate cancer in the nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes obtained from the subject.

The function of the encoded protein (which may be impaired or absent when alterations are present) is preferably the normal biologic activity of that protein within the body of the subject when the gene encoding the protein is not altered. For example, many of the proteins from the genes described herein play a role in DNA damage repair, or in the androgen receptor signal pathway. Thus, for example, a DNA damage repair protein having an alteration that impairs its function (e.g., results in a truncation of the expressed protein) may no longer have DNA damage repair activity. A DNA damage repair protein lacking such an alteration has normal DNA damage repair activity.

From the subject, the nucleic acid to be screened may be from any tissue or cell in which genomic DNA or a genomic DNA sequence may be obtained. Non-limiting examples include blood, hair, and buccal tissue or cells. Peripheral blood is preferred. Lymphocytes from the peripheral blood are preferred.

The methods may include the step of obtaining the tissue sample, and may include the step of obtaining the nucleic acid, and may include the step of obtaining a cell nucleus. The nucleic acid may be any nucleic acid that has, or from which may be determined, the presence and/or quantity of genomic instability or double stranded DNA breaks, and the cell or nucleus may be any cell or nucleus that has, or from which may be determined, the presence and/or quantity of gamma-H2AX foci. The nucleic acid may be any nucleic acid that has, or from which may be obtained, the germline nucleic acid sequence of one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes, or the complement thereof, or any portion thereof. For example, the nucleic acid may be chromosomal or genomic DNA, may be mRNA, or may be a cDNA obtained from the mRNA. The sequence of the nucleic acid may be determined using any sequencing method suitable in the art.

In some detailed aspects, the methods comprise hybridizing nucleic acids. For example, such methods may comprise the steps of contacting, preferably under stringent conditions, a nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes obtained from the subject with one or more polynucleotide probes that have a nucleic acid sequence complementary to one or more of an AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 nucleic acid sequence having one or more alterations that predispose a subject to develop prostate cancer, and determining whether the one or more probes hybridized with the nucleic acid comprising one or more of AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes obtained from the subject. The methods may comprise the step of diagnosing whether the subject has a predisposition to develop prostate cancer based on whether the probes have hybridized with the nucleic acid.

The probes may comprise a detectable label. The nucleic acid obtained from a subject may be labeled with a detectable label. Detectable labels may be any suitable chemical label, metal label, enzyme label, fluorescent label, radiolabel, fluorochromes, electrochemiluminescent probes, quantum dots, fluorescent proteins, luminescent proteins, or any combination thereof. The methods may comprise detecting the detectable label on probes hybridized with the nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes. The probes may be affixed to a support, such as an array. For example, a labeled nucleic acid obtained from a subject may be contacted with an array of probes affixed to a support. The probes may include any probes described or exemplified herein.

In some detailed aspects, the hybridization may be carried out in situ, for example, in a cell obtained from the subject. For example, the methods may comprise contacting (preferably under stringent conditions) a cell comprising a nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes obtained from the subject, or contacting (preferably under stringent conditions) a nucleic acid in the cell, with one or more polynucleotide probes comprising a nucleic acid sequence complementary to an AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 nucleic acid sequence having one or more alterations that predispose a subject to develop prostate cancer and determining whether the one or more probes hybridized with the nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes in the cell. The methods may comprise the step of diagnosing whether the subject has a predisposition to develop prostate cancer based on whether the probes have hybridized with the nucleic acid. The probes may comprise a detectable label, and the method may comprise detecting the detectable label on probes hybridized with the nucleic acid comprising one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes. Detectable labels may be any suitable chemical label, metal label, enzyme label, fluorescent label, radiolabel, fluorochromes, electrochemiluminescent probes, quantum dots, fluorescent proteins, luminescent proteins, or any combination thereof.

In any of the hybridization assays, the probes may be DNA or RNA, are preferably single stranded, and may have any length suitable for avoiding cross-hybridization of the probe with a second target having a similar sequence with the desired target. Suitable lengths are recognized in the art as from about 20 to about 60 nucleotides optimal for many hybridization assays (for example, see the Resequencing Array Design Guide available from Affymetrix: www.affymetrix.com/support/technical/ byproduct.affx?product=cseq), though any suitable length may be used, including shorter than 20 or longer than 60 nucleotides. It is preferred that the probes hybridize under stringent conditions to the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 nucleic acid sequence of interest. It is preferred that the probes have 100% complementary identity with the target sequence.

The methods described herein, including the hybridization assays, whether carried out in vitro, on an array, or in situ, may be used to determine any alteration in one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 germline nucleic acid sequence that has a known or suspected association with predisposing a subject to genomic instability and/or to develop prostate cancer, including any of those described or exemplified herein. In any of the methods described herein, the alterations may be, for example, a mutation or variation in the germline nucleic acid sequence relative to a germline nucleic acid sequence that has no known or suspected association with predisposing a subject to develop prostate cancer. The alteration may comprise one or more nucleotide substitutions, an addition of one or more nucleotides in one or more locations, a deletion of one or more nucleotides in one or more locations, an inversion or other DNA rearrangement, or any combination thereof. The alteration may encode a stop signal where a stop signal is not present in a healthy or non-altered form of the gene. A substitution may, but need not, change the amino acid sequence of the protein encoded by the gene. Any number of substitutions, additions, or deletions of nucleotides are possible. The alteration may occur in an intron, an exon, or both, or may occur at a splice site. The alteration may comprise any alteration described or exemplified herein, including those listed in Table 3 and Table 4.

The polynucleotide probes used in nucleic acid hybridization aspects may comprise a portion of one or more of AKR1C1 (SEQ ID NO: 79), PALB2 (SEQ ID NO: 68), APTX (SEQ ID NO: 48), BLM (SEQ ID NO: 70), BRCA1 (SEQ ID NO: 49), CTBP1 (SEQ ID NO: 62), DDB2 (SEQ ID NO: 80), FANCA (SEQ ID NO: 69), FANCL (SEQ ID NO: 56), MBD5 (SEQ ID NO: 61), MSH3 (SEQ ID NO: 57), NEIL3 (SEQ ID NO: 50), RAD51D (SEQ ID NO: 96), RAD54L2 (SEQ ID NO: 59), SP1 (SEQ ID NO: 90), TP53BP1 (SEQ ID NO: 83), UBE2D3 (SEQ ID NO: 76), UBE2V2 (SEQ ID NO: 88), NRIP1 (SEQ ID NO: 60), EFCAB6 (SEQ ID NO: 51), CRISP3 (SEQ ID NO: 67), PAPSS2 (SEQ ID NO: 53), ATP6V0A2 (SEQ ID NO: 58), ALG13 (SEQ ID NO: 75), MGAT2 (SEQ ID NO: 84), B3GAT3 (SEQ ID NO: 91), DOLK (SEQ ID NO: 92), FLT3 (SEQ ID NO: 93), ASXL1 (SEQ ID NO: 89), KDR (SEQ ID NO: 72), and/or NOTCH2 (SEQ ID NO: 95), or complement thereof, which portion contains the genomic instability and/or prostate cancer risk-associated alteration. These sequence identifiers correspond to the Genbank Accession number associated with the cDNA sequence of each respective gene. These sequence identifiers (or complement thereof) may, for example, serve as a reference sequence for a gene having no alterations associated with prostate cancer predisposition.

Determination of whether a subject has genomic instability, double stranded DNA breaks, and/or enhanced gamma-H2AX foci, and/or one or more of the altered genes described or exemplified herein may serve as a determination of whether the subject has a predisposition to develop prostate cancer. These determinations may also be used to determine whether the subject has prostate cancer, or may be used as an adjunct to another test that establishes that the subject has prostate cancer, for example, as a confirmation test. Thus, in some aspects, the assessments are followed by a treatment protocol, which treatment protocol inhibits or prevents the development of prostate cancer, or which treats prostate cancer.

For example, if the subject is determined to have genomic instability, double stranded DNA breaks, and/or enhanced gamma-H2AX foci, and/or determined to have one or more alterations in the one or more genes, which alterations are associated with the disposition to develop prostate cancer, but not determined to have prostate cancer, then the subject may be treated with a treatment regimen capable of inhibiting the onset of prostate cancer, for example, a type of prostate cancer derived from impaired DNA damage repair or of prostate cancer derived from impaired androgen signaling. Optionally, the subject may also be treated with a monitoring regimen, which includes more frequent or aggressive monitoring relative to the normal prostate cancer monitoring in the general population. Such enhanced monitoring is carried out beyond the normal standard of care for the general population.

The treatment regimen may include a prostatectomy, even though the subject does not have prostate cancer. The treatment regimen may include androgen deprivation therapy, even though the subject does not have prostate cancer. Androgen deprivation may optionally be used in combination with a prostatectomy, even though the subject does not have prostate cancer. It is believed that such interventions, normally reserved for prostate cancer patients, may have a beneficial effect in inhibiting prostate cancer development in subjects determined to have a high probability of developing prostate cancer. In some aspects, the treatment regimen comprises administering to the subject an effective amount of a compound or pharmaceutical composition capable of delaying or inhibiting the onset of prostate cancer. In some aspects, the treatment regimen may comprise administering to the subject a PARP inhibitor, even though the subject does not have prostate cancer. In some aspects, the treatment regimen comprises one or more of diet management, vitamin supplementation, nutritional supplementation, exercise, psychological counseling, social counseling, education, and regimen compliance management.

If the subject is determined to have genomic instability, double stranded DNA breaks, and/or enhanced gamma-H2AX foci, and/or determined to have one or more alterations in the one or more genes, which alterations are associated with the disposition to develop prostate cancer, and also determined to have prostate cancer, then the subject may be treated with a treatment regimen capable of treating the prostate cancer, including inhibiting metastasis or further progression of the cancer. The treatment regimen may include a prostatectomy. The treatment regimen may include androgen deprivation therapy. The treatment regimen may include a prostatectomy and androgen deprivation therapy in combination. The treatment regimen may (further) include DNA damage therapy, including coupling DNA damage with treatments that override DNA damage checkpoint controls, such as U.S. application Ser. No. 14/564,186, incorporated by reference herein. The treatment regimen may include administration of chemotherapeutic or chemopreventive agents, including PARP inhibitors. In some aspects, the treatment regimen comprises one or more of diet management, vitamin supplementation, nutritional supplementation, exercise, psychological counseling, social counseling, education, and regimen compliance management.

The invention also features systems for diagnosing a predisposition to develop prostate cancer. The systems may comprise, for example, an immunoblotting support, an immunofluorescence support, an immunohistochemistry support, an ELISA support, or a flow cytometry support comprising peripheral blood lymphocytes obtained from a human subject, permeabilized, and treated with a DNA damaging agent or DNA damaging amount of radiation, a detectably-labeled antibody that specifically binds to gamma-H2AX foci, and a detector capable of detecting the detectably-labeled antibody bound to gamma-H2AX foci in the lymphocytes and of quantifying the level of gamma-H2AX foci in the lymphocytes based on detection of the detectably-labeled antibody, optionally, a metaphase spread or a karyotype obtained from the lymphocytes, and a detector capable of detecting the absence or presence and type of genomic instability from the metaphase spread or karyotype, a computer comprising an input for entering the level of gamma-H2AX foci in the lymphocytes and the type of genomic instability in the lymphocytes, a data structure comprising reference values for a level of gamma-H2AX foci and a type of genomic instability that together indicate a predisposition to develop prostate cancer, a processor operably connected to the data structure, wherein the processor is programmed to compare the level of gamma-H2AX foci and type of genomic instability detected in the lymphocytes with the reference values and generate a diagnosis of whether the subject has or does not have a predisposition to develop prostate cancer based on the comparison of the level of gamma-H2AX foci in the lymphocytes and the type of genomic instability in the lymphocytes with the reference values, and an output for providing the diagnosis to a user.

The systems may comprise a data structure comprising one or more reference nucleic acid sequences having one or more alterations in one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes associated with predisposing a subject to develop prostate cancer, and a processor operably connected to the data structure. The data structure may comprise one or more reference nucleic acid sequences that do not have any alterations in one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2. The processor is preferably capable of comparing, and preferably programmed to compare determined nucleic acid sequences (for example, those determined from nucleic acids obtained from a subject) with reference nucleic acid sequences.

Optionally, the system may comprise an input for accepting determined nucleic acid sequences obtained from tissue samples from a subject. Optionally, the system may comprise an output for providing results of a sequence comparison to a user such as the subject, or a technician, or a medical practitioner. Optionally, the system may comprise a sequencer for determining the sequence of a nucleic acid such as a nucleic acid obtained from a subject. Optionally, the system may comprise a detector for detecting a detectable label on a nucleic acid.

Optionally, the system may comprise computer readable media comprising executable code for causing a programmable processor to determine a diagnosis of the subject, for example whether the subject has a predisposition to develop prostate based on whether or not a nucleic acid obtained from the subject includes a sequence alteration associated with a predisposition to develop prostate cancer (e.g., encodes a protein with impaired function or with substantially no function). The diagnosis may be based on the comparison of determined nucleic acid sequences with reference nucleic acid sequences. The diagnosis may be based on a determination of hybridization of a nucleic acid probe with a nucleic acid obtained from the subject. Thus, the system may comprise an output for providing a diagnosis to a user such as the subject, or a technician, or a medical practitioner. Optionally, the system may comprise computer readable media that comprises executable code for causing a programmable processor to recommend a treatment regimen for the subject, for example, a treatment regimen for preventing, inhibiting, or delaying the onset of prostate cancer, or for treating prostate cancer.

In any of the systems, a computer may comprise the processor or processors used for determining information, comparing information and determining results. The computer may comprise computer readable media comprising executable code for causing a programmable processor to determine a diagnosis of the subject. The systems may comprise a computer network connection, including an Internet connection.

The invention also provides computer-readable media. In some aspects, the computer-readable media comprise executable code for causing a programmable processor to compare the nucleic acid sequence of one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes determined from a nucleic acid obtained from a tissue sample obtained from a subject with one or more reference nucleic acid sequences having one or more alterations in one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes sequence associated with predisposing a subject to develop genomic instability and/or to develop prostate cancer. The alterations may be any alteration described or exemplified herein. Optionally, the computer-readable media comprise executable code for causing a programmable processor to compare the nucleic acid sequence of one or more of the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 genes determined from a nucleic acid obtained from a tissue sample obtained from a subject with one or more reference nucleic acid sequences that do not have any alterations in the AKR1C1, PALB2, APTX, BLM, BRCA1, CTBP1, DDB2, FANCA, FANCL, MBD5, MSH3, NEIL3, RAD51D, RAD54L2, SP1, TP53BP1, UBE2D3, UBE2V2, NRIP1, EFCAB6, CRISP3, PAPSS2, ATP6V0A2, ALG13, MGAT2, B3GAT3, DOLK, FLT3, ASXL1, KDR, and/or NOTCH2 gene sequences. The computer readable media may comprise a processor, which may be a computer processor.

The systems and computer readable media may be used in any of the methods described or exemplified herein, for example, methods for diagnosing a predisposition to develop prostate cancer. For example, the systems and computer readable media may be used to facilitate comparisons of gene sequences, or to facilitate a diagnosis.

The methods, systems, and computer readable media comprise various reference values. For example, the reference values comprise certain quantities such as a quantity of gamma-H2Ax or a quantity of double stranded DNA breaks, and comprise certain qualities such as the presence or absence of a type of polymorphism in a gene sequence or the presence or absence of a type of genomic instability such as chromosomal aneuploidy. In general, such reference values may be established according to studies of individuals and/or studies of populations. It is contemplated that, over time, as more and more individuals and larger populations are studied, the reference values, particularly the quantitative reference values, may become more precise or established to have a greater confidence. Reference value quantities may comprise quantities based on available information for any given period of time.

The following examples are provided to describe the invention in greater detail. They are intended to illustrate, not to limit, the invention.

EXAMPLE 1

Materials and Methods

Patient selection. Case-only prostate cancer patients included in this study (n=12) had undergone evaluation for inherited cancer risk. These patients had family cancer history meeting criteria for specific hereditary cancer syndromes with no mutations detected in the corresponding genes. Hereditary cancer syndromes evaluated in these families included hereditary breast-ovarian cancer (HBOC), Lynch syndrome (LS), and hereditary prostate cancer (HPC). No pathogenic mutations were identified from sequencing the following genes (BRCA1, BRCA2, MLH1, MSH2, PMS2, MSH6, and HOXB13). These patients had consented to the in-house Risk Assessment Program Registry, which allowed further research genomic sequencing. All patients reported being white, non-Hispanic. Peripheral blood DNA from these 12 prostate cancer patients was sent for exome sequencing.

Exome sequencing. Exome sequencing of germline DNA was performed at 30X average coverage using a VCRome kit (Roche Nimblegen, Madison Wis.) for library preparation, indexing and 100 bp paired end processing using the Hiseq platform (Illumina, Hayward, Calif.). Human hg19 reference-guided alignment and variant calling were done using the Illumina CASAVA software pipeline. Heuristic filtering processes were applied to remove variants that fall into non-coding regions, with synonymous effect, or common variants found in the 1000 genomes, dbSNP or Exome Sequencing Project (ESP) database. The Ambry Variant Analyzer (AVA™) produced candidate mutation short lists of rare variants by restricting to variants fitting a dominant/recessive model of inheritance, as well a listing of variants associated with hereditary and somatic cancers, regardless of frequency.

Development of a high value list of candidate genes. The candidate gene list was assembled from the sources listed in Table 1. Genes collected from various sources were pre-screened for possible aliases by using G-convert from G-profiler (biit.cs.ut.ee/gprofiler/gconvert.cgi) in batch mode to ensure use of official gene symbols with Entrez ID numbers. Manual curation using (www.genenames.org) from the Human Genome Organization (HUGO) Gene Nomenclature Committee (HGNC) was done when G-convert did not return information. PCAP, PCA3 and HPC6, which were listed as loci relevant to prostate cancer by at least one source, were not included as they fall under the HGNC locus type "phenotype only", indicating the causative gene has not been identified. Non-coding transcripts such as PCAT4, 5 and 6 and pseudogenes were excluded.

TABLE 1

| Sources for building the candidate gene list. | |
| --- | --- |
| Description | Number of genes |
| DNA repair genes | 179 |
| AR-regulated DNA repair genes | 144 |
| AR interactors | 149 |
| BRCA1 interactors | 102 |
| Genes most frequently mutated in prostate tumors | 19 |
| TARGET | 130 |
| Genes linked to androgen and estrogen biosynthesis and metabolism | 30 |
| Literature mining for genes involved in prostate cancer | Top 50 Top 150 |
| Candidate genes list for exome study of LNCaP cell line | Top 50 |
| Genes linked to glycosylation disorders | 103 |

Variant selection. By analysis through its AVA™ filtering software, lists of rare variants (defined as frequency less than 1% in the general population) were prepared for each patient. From these combined lists, 84 single nucleotide variations (SNVs) with more than 3 reads and Q score above 25 and leading to non-synonymous changes at the protein level in candidate genes were extracted. Variants leading to non-synonymous changes in encoded proteins were selected if they received scores indicating a protein-damaging function with at least 3 of 5 in silico predictors (PolyPhen-2 with HumDiv as model classifier, SIFT, PROVEAN, Mutation-Assessor, and MutationTaster). The conversion of the calls made by each predictor into neutral vs. non-neutral was made using an approach that integrates different predictive algorithms. For PolyPhen-2, "probably damaging" and "possibly damaging" were considered non-neutral. For MutationAssessor, "high" and "medium" were considered non-neutral. For MutationTaster, "disease causing" and "disease causing_automatic" were considered non-neutral and "polymorphism" and "polymorphism_automatic" neutral. "Damaging" (SIFT) and "deleterious" (PROVEAN) were considered non-neutral while "tolerated" (SIFT) and "neutral" (PROVEAN) were considered neutral. For Mutation-Taster, 0.99 was used as cut-off in the disease_causing category.

In-frame deletion (Indel) variants were characterized with PROVEAN and MutationTaster. Indels that had a length divisible by 3 and caused amino acid insertion/deletion (also called 3N indels) were also analyzed with SIFT-Indel (sift-dna.org). Variants associated with possible splicing defects were also selected. Mutalyzer 2.0.4 (mutalyzer.nl) was used to ascertain that the variants were described according to the Human Genome Variation Society (HGVS) nomenclature, effectively matching described amino acid and nucleotide coordinates to the GRCh37/hg19 assembly.

Variant verification. The Exome Aggregation Consortium (ExAC) website, Cambridge, MA. (version 0.3) (exac.broadinstitute.org) was used to assess the frequency of the selected variants in the general population or in a particular ethnic group. The ExAC data set contains information on 60,706 unrelated individuals sequenced as part of various disease-specific and population genetic studies, approximately 50% of who are of European non-Finnish ancestry. A second independent group of controls, referred to as ITMI genomes, consisted of 634 white non-Hispanic individuals who denied a personal or family history of cancer. For all variants with predicted possible damaging consequences for protein function, primers flanking the variation were designed to amplify a product of ~200 to 400 base pairs. After digestion with ExoSap-IT (Affymetrix, Santa Clara, CA), the PCR product was sent to Genewiz (South Plainfield, NJ) for Sanger sequencing.

Molecular modeling. For analysis of structural consequences of missense variants, models of PAPSS2 and AKR1C1 were generated. All molecular display figures were prepared with the UCSF Chimera software. While the N-terminal kinase domain is of known structure (2AX4), a full-length model of PAPSS2 was generated with Biological Assembly Modeler based on the closest homolog of known structure, PAPSS1 (PDB code 1XNJ, 77% identity, 87% similarity), and compared with a previously deposited model. An alternate template structure (2QJF) was superposed to extract the placement of the substrate and product molecules, (ADP and Adenosine-5'-phosphosulfate).

Lymphocyte cell preservation, culture, and analysis of DNA damage response (DDR). Peripheral blood lymphocytes (PBLs) were available from 9/12 of the exome sequenced patients and 10 age-matched and gender-matched individuals without a cancer diagnosis or a family history of cancer. Control samples were obtained from the FCCC Biosample Repository Facility. For analysis of DDR, cells were cultured in RPMI-1640 containing 15% fetal bovine serum (HyClone Laboratories, Logan, UT), 2 mM L-glutamine (Life Technologies, Grand Island, N.Y.), 50 μM 2-mercaptoethanol (Sigma-Aldrich, St. Louis, MO), 0.2 units human recombinant insulin (Sigma) per ml, 50 units penicillin and 50 mg streptomycin per ml (complete RPMI), and then stimulated with phytohemagglutinin (PHA)-M (Life Technologies, Grand Island, NY) and recombinant human interleukin 2 (IL-2) (NCI Preclinical Repository) for 72 hours. Cells were then treated with vehicle, 10 μM aphidicolin, or 25 μM etoposide, and fixed in paraformaldehyde 2 hours later. For immunofluorescence, cells were allowed to attach to poly-d-lysine-coated 96-well plates, stained with anti-γH2AX antibody (#05-636, Millipore, Temecula, CA). Sixteen images per well were acquired at 20X (with each image acquired in 2 channels to detect γH2AX with TRITC and total DNA with DAPI) utilizing the ImageXpress micro automated microscope (Molecular Devices, Sunnyvale, CA) driven by MetaXpress software. Images were analyzed in the Multiwavelength Scoring module of MetaXpress and results were displayed and exported utilizing the AcuityXpress software package (Molecular Devices, Sunnyvale, CA).

EXAMPLE 2

Results

Patient cohort. Patient and family cancer characteristics of 12 unrelated participants with prostate cancer undergoing exome analysis are shown in Table 2. The mean age at prostate cancer diagnosis was 57.8 years (range 41-68 years). Fifty-eight percent had Gleason score >=7, and 25% had advanced stage disease (T3). Each participant had a strong family cancer history, with either multiple first-degree or second-degree relatives with prostate or other cancers.

TABLE 2

| | | | Family history and prostate cancer characteristics of analyzed prostate cancer patients. | |
| --- | --- | --- | --- | --- |
| Patient ID | Age at diagnosis | Stage/Gleason | 1$^{st}$ degree relatives with cancer Type of cancer/age | 2$^{nd}$ degree relatives with cancer Type of cancer/age |
| 112940 | 68 | T2aN0MX/3 + 4 = 7 | sister-ovary 27 and colon 66 sister-abdominal cancer early 60's brother-prostate 59 mother-brain 52 father-unknown cancer | |
| 117197 | 68 | T3bN0MX/4 + 3 = 7 | mother-stomach 80, colon 95 | nephew-non Hodgkin's 20's maternal uncle-unknown cancer maternal grandmother-colon 69 paternal uncle-prostate 62 paternal uncle-mouth 88 |
| 117939 | 65 | T2cNOMX/3 + 3 = 6 | father-prostate 65 2 siblings w polyps | paternal uncle-throat 60 paternal uncle-prostate 65 maternal grandmother- breast 30 nephew-small cell desmoplastic tumor 28 |
| 123136 | 59 | T2cNXMX/6 | mother-colon mid 40's father-lung 59 daughter-melanoma 25 | |
| 124604 | 44 | T2cN0MX/3 + 3 = 6 | father-melanoma 72, polyps | paternal uncle-colon 50 maternal uncle-prostate cancer 62 maternal uncle- prostate cancer 55 maternal grandfather- prostate cancer 88 |
| 124853 | 65 | T2cNOMX/3 + 3 = 6 | sister-basal cell 60 mother-stomach 59 | paternal aunt- breast paternal cousin's daughter- ovarian 50's |

TABLE 2-continued

| | | | Family history and prostate cancer characteristics of analyzed prostate cancer patients. | |
|---|---|---|---|---|
| Patient ID | Age at diagnosis | Stage/Gleason | $1^{st}$ degree relatives with cancer Type of cancer/age | $2^{nd}$ degree relatives with cancer Type of cancer/age |
| 125671 | 54 | T2cN0MX/3 + 3 = 6 | sister-uterine 54 sister-non Hodgkin's 37 father-prostate 72 mother-kidney 76 | paternal cousin-breast 36 paternal cousin-colon 58 maternal uncle-unknown cancer 30 |
| 126002 | 59 | T3aN0MX/3 + 4 = 7 and 4 + 3 = 7 and 6 (multiple areas) | | maternal aunt-unknown cancer 89 maternal cousin - colon 65 maternal cousin-brain 50's maternal 1st cousin-leukemia 7-breast/skin 40's paternal 1st cousin-brain 59 |
| 129413 | 57 | T1c/3 + 4 = 7 | father-prostate 70, kidney 80, liver 80 sister-precancerous uterine 47 | paternal grandfather-prostate 85 paternal great-grandfather- stomach paternal uncle-prostate 66 |
| 129547 | 62 | T2cN0MX/3 + 4 = 7 | sister-ovary 57, cervix 57 | paternal cousin-inflammatory breast 45 maternal uncle-prostate 78 maternal uncle -prostate 78 maternal ½ uncle- pancreas 56 maternal ½ uncle- prostate 78 2 maternal cousins-unknown cancer |
| 129748 | 41 | T3bN1M0/4 + 4 = 8 | father-prostate 67 | paternal grandfather-polyps paternal great aunt-breast 30's |
| 131534 | 52 | T2cNO/3 + 4 = 7 | mother-breast 68, melanoma 65 father-prostate 70 | maternal aunt-colon 45 maternal aunt-polyps 40 maternal cousin-glioblastoma 26 paternal grandmother-lung |

Development of a high value list of candidate genes. To meet the goal of developing an operational framework for assessing case-only patients, a comprehensive, hypothesis-based candidate gene list was developed. To this end, top scoring candidates were integrated from a number of existing sources that collated genes based on orthogonal selection criteria (Table 1). The primary hypothesis for this purpose was that rare variants leading to defects in DDR would be important in predisposition for general cancer risk, while the secondary hypothesis was that rare variants damaging genes associated with androgen signaling or prostate function would provide a bias for cancer in the prostate.

To identify a relevant candidate set the Wood group website, which maintains an updated comprehensive list of genes linked to DNA damage response, was queried. Wood R D, et al. (2001) Science 291:1284-9. This list was extended with genes described by Polkinghorn and colleagues, who have noted a subset of DNA repair genes specifically regulated by the androgen receptor (AR). Polkinghorn WR, et al. (2013) Cancer Discov. 3:1245-53. See FIG. 2A. The Human Protein Reference Database (HPRD) provided lists of genes that interacted physically or functionally with the well-validated risk factor BRCA1, as well as the AR. Providing broader context relevant to AR signaling, several recent studies have provided lists of genes mutated at appreciable frequencies in sporadic prostate cancer, including castration resistant prostate cancer. The TARGET database (Tumor Alterations Relevant for Genomics-Driven Therapy) provides a broader list of genes of clinical value for cancer treatment, based on their roles as tumor drivers. Sun and colleagues developed a list of single nucleotide polymorphisms (SNPs) affecting sex hormone metabolism, some of which showed significant or near-significant linkage to prostate cancer aggressiveness at diagnosis Sun T et al. (2011) Cancer Prey. Res. (Phila) 4:2044-50. Eight hundred twenty six genes were obtained by compiling these and additional sources as of particular interest for potential involvement in hereditary prostate cancer, with the significant majority of these genes nominated by more than one of the sources.

Finally, as a tertiary hypothesis, it was also considered that non-rare variants, or variants in genes linked to cancers other than prostate, might contribute to prostate cancer risk in some circumstances. Typically, a threshold of 1% for a minor frequency allele (MAF) is used to filter out non-rare variants as insignificant in the absence of clear clinical indication of phenotypic effect. However, a growing body of evidence suggests that cancer risk reflects the interaction of multiple predisposing factors, suggesting such non-rare variants may interact with specific rare variants. The analysis also took into account non-rare variants in genes predicted as relevant to somatic or hereditary cancers.

Identification of genetic variants in the prostate cancer patient cohort. Focusing on this candidate list, rare single nucleotide variants (SNVs) causing missense mutations, frameshift or nonsense mutations predicted to result in early truncation of protein and short in-frame insertions or deletions (indels) were analyzed. SNVs were only considered further if they passed an initial test in which multiple predictor algorithms indicated the variant would disrupt protein function.

Table 3 summarizes the significant variants found in each of the 12 patients (with extended information in Table 4). All variants listed in Table 3 passed Sanger validation. Each patient had variants affecting 3 to 7 genes on the candidate list. All 12 patients had reported being white and non-Hispanic: Table 3 describes the frequency of each variant in the subset of ~30,000 European non-Finnish individuals of the Exome Aggregation Consortium (ExAC) database; these frequencies were in agreement with those reported in an independent (ITMI) cohort of 634 white non-Hispanic individuals who denied a personal or family history of cancer (Table 4). Thirty of the changes identified in the prostate cancer patients in this study were found in fewer than 20 individuals in the ExaC database (<0.0003%), with 10 never previously reported. In addition, a number of non-rare variants in genes relevant to cancer risk (e.g., in BRCA1, PALB2, BLM, and others) were detected in a significant number of individuals.

TABLE 3

Selected variants with scores of amino acid damage from
5 predictors and variant frequency in ExAC, by patient.

| Patient ID | Variant DNA level | Gene | Consequence | Non-neutral scores | Representation in ExAC (European non-Finnish) | |
|---|---|---|---|---|---|---|
| | | | | | Allele count | Allele number |
| 112940 | 9:32989766 G/A | APTX | NP_001182178.1 p.R56X | 5* | 0 | 66736 |
| | 17:41246481 T/C | BRCA1 | NP_009225.1 p.Q356R | 4 | 4198 | 66734 |
| | 4:178274801 T/G | NEIL3 | NP_060718.2 p.F460C | 3 | 10 | 66730 |
| 117197 | 22:43933284 CCT/C | EFCAB6 | NP_073622.2 p.Q1340Rfs*43 | 5* | 606 | 66684 |
| | 2:38301879 T/A | CYP1B1 | NP_000095.2 p.D218V | 5 | 15 | 41314 |
| | 10:89503283 C/T | PAPSS2 | NP_004661.2 p.P454L | 5 | 0 | 66732 |
| | 17:41246481 T/C | BRCA1 | NP_009225.1 p.Q356R | 4 | 4198 | 66734 |
| | 9:135779052 G/A | TSC1 | NP_000359.1 p.H732Y | 4 | 350 | 66706 |
| 117939 | 1:156212872 T/A | BGLAP | NP_954642.1 p.C74X | 5* | 8 | 66696 |
| | 2:58386928 G/GTAAT | FANCL | NP_060532.2 p.T367Nfs*13 | 5* | 232 | 65648 |
| | 5:80109533 T/C | MSH3 | NP_002430.2 p.I929T | 5 | 0 | 66740 |
| | 12:124209215 G>T | ATP6V0A2 | NP_036595.2 p.K103N | 5 | 15 | 66734 |
| | 3:51673972 A/T | RAD54L2 | NP_055921.2 p.I730F | 4 | — | — |
| | 21:16340242 T/C | NRIP1 | NP_003480.2 p.E91G | 4 | — | — |
| | 2:149226489 C/T | MBD5 | NP_060798.2 p.A326V | 3 | — | — |
| 123136 | 4:1206089 G/A | CTBP1 | NP_001319.1 p.421L | 4 | 28 | 14670 |
| | 3:38888684 A/T | SCN11A | NP_054858.2 p.F1626Y | 3 | — | — |
| | 1:63876815 A/G | ALG6 | Splice acceptor (−2) | — | — | — |
| | 1:120056817 T/TGCA | HSD3B1 | NP_000853.1 p.V224_Y225insH | — | 2 | 66708 |
| | 4:153332604 TCTC/T | FBXW7 | NP_361014.1 p.E117del | — | 35 | 66114 |
| 124604 | 16:23634293 C/T | PALB2 | NP_078951.2 p.G998E | 5 | 1430 | 66736 |
| | 16:89815152 G/A | FANCA | NP_000126.2 p.S1088F | 4 | 4798 | 65430 |
| | 15:91326099 C/T | BLM | NP_000048.1 p.P868L | 4 | 4239 | 66162 |
| | 6:49700908 G/A | CRISP3 | NP_006052.1 p.A197V ** | 2 | 0 | 66362 |
| 124853 | 18:3452067 G/A | TGIF1 | NP_733796.2 p.W30X | 5* | 33 | 66002 |
| | 4:55955969 C/T | KDR | NP_002244.1 p.A1065T ** | 5 | 52 | 66726 |
| | 17:12901781 A/C | ELAC2 | NP_060597.4 p.S490A | 5 | 39 | 66734 |
| | 19:50766628 C/T | MYH14 | NP_001139281.1 p.A882V | 3 | 23 | 27644 |
| | X:110973633 TGAA/T | ALG13 | NP_001093392.1 p.E795del | — | 33 | 41558 |
| | 4:103747794 C/T | UBE2D3 | Splice acceptor (−1) | — | — | — |
| 125671 | 9:35707745 G/C | TLN1 | NP_006280.3 p.L1539V | 4 | 13 | 66734 |
| | 1:145578236 C/T | PIAS3 | NP_006090.2 p.R67W | 3 | 13 | 66740 |
| | 10:5014483 T/A | AKR1C1 | NP_001344.2 p.S221N | 3 | 119 | 66712 |
| | 10:5014484 C/A | AKR1C1 | | | 119 | 66712 |
| | 11:47237894 CAGA/C | DDB2 | NP_000098.1 p.R47del | — | — | — |
| 126002 | 17:35564593 G/A | ACACA | NP_942134.1 p.R1182W | 5 | 16 | 66612 |
| | 17:41246481 T/C | BRCA1 | NP_009225.1 p.Q356R | 4 | 4198 | 66734 |
| | 7:18633593 A/G | HDAC9 | NP_001191074.1 p.Y199C | 3 | 0 | 66702 |
| 129413 | 14:50088465 T/G | MGAT2 | NP_002399.1 p.I160S | 5 | 610 | 66402 |
| | 17:41246481 T/C | BRCA1 | NP_009225.1 p.Q356R | 4 | 4198 | 66734 |
| | 15:43762077 TGGGATA/T | TP53BP1 | NP_001135451.1 p.I455_P456del | — | — | — |
| 129547 | 2:38298287 T/TGGTGGCATCA | CYP1B1 | NP_000095.2 p.T404Sfs*30 | 5* | *** | |
| | 10:94297192 C/T | IDE | NP_004960.2 p.G72S | 5 | 8 | 66724 |
| | 12:124824917 C/T | NCOR2 | NP_001070729.2 p.R1794Q | 3 | 2 | 65378 |
| | 21:16337279 C/A | NRIP1 | NP_003480.2 p.V1079F | 3 | 44 | 66670 |
| 129748 | 16:23632788 TTTTC/T | PALB2 | NP_078951.2 p.E1002Tfs*4 | 5* | — | — |
| | 6:52657698 C/T | GSTA1 | NP_665683.1 p.E168K | 4 | 1 | 66738 |
| | 8:48973252 G/A | UBE2V2 | NP_003341.1 p.R101Q | 4 | 1 | 65850 |
| | 20:31021718 C/T | ASXL1 | NP_056153.2 p.R573W ** | 4 | 4 | 63434 |
| | 12:53776449 G/C | SP1 | NP_612482.2 p.G240R | 3 | 26 | 66738 |
| | 11:62388048 G/C | B3GAT3 | NP_036332.2 p.R60G | 3 | 1 | 60290 |
| 131534 | 9:131709581 A/AT | DOLK | NP_055723.1 p.M1? | 5* | 823 | 63350 |
| | 13:28592620 T/C | FLT3 | NP_004110.1 p.Y842C | 5 | 2 | 66710 |
| | 10:94274700 A/G | IDE | NP_004960.2 p.M254T | 5 | 11 | 66698 |
| | 4:70723282 C/G | SULT1E1 | NP_005411.1 p.W27C | 4 | — | — |
| | 1:120478125 A/C | NOTCH2 | NP_001186930.1 p.F1209V | 4 | 306 | 66726 |

TABLE 3-continued

Selected variants with scores of amino acid damage from
5 predictors and variant frequency in ExAC, by patient.

| Patient ID | Variant DNA level | Gene | Consequence | Non-neutral scores | Representation in ExAC (European non-Finnish) | |
|---|---|---|---|---|---|---|
| | | | | | Allele count | Allele number |
| | 17:33430313 T/C | RAD51D | NP_001136043.1 p.E223G | 4 | 874 | 51128 |
| | 1:182555767 C/T | RNASEL | NP_066956.1 p.G59S | 4 | 379 | 66514 |

5* score given to variant creating stop gain or frameshift;
** variant causing missense and located in splice site;
*** this variant has been described in patients with congenital glaucoma, an autosomal recessive trait usually recognized during the first year of life.
The mutation is not listed in ExAC as it excludes mutations associated with severe pediatric diseases. In the representation in the ExAC column, (—) denotes that the variant was not found in the database while (0) denotes that the variant was absent in European non-Finnish but detected in other ethnicities.

TABLE 4

Full variant description.

| Variant DNA level | Gene | Variant cDNA level | Variant protein level | Variant class |
|---|---|---|---|---|
| 9:32989766 G/A (rs201912053) | APTX | NM_001195249.1:c.124C>T | NP_001182178.1 p.R56X | Stop gain |
| 17:41246481 T>C (rs1799950) | BRCA1 | NM_007294.3:c.1067A>G | NP_009225.1 p.Q356R | Missense |
| 4:178274801 T/G (rs145637230) | NEIL3 | NM_018248.2:c.1379T>G | NP_060718.2 p.F460C | Missense |
| 22:43933284 CCT/C (rs149931639) | EFCAB6 | NM_022785.3:c.4019_4020del | NP_073622.2 p.Q1340Rfs*43 | Frameshift |
| 2:38301879 T/A (rs724549383) | CYP1B1 | NM_000104.3:c.653A>T | NP_000095.2 p.D218V | Missense |
| 10:89503283 C/T | PAPSS2 | NM_004670.3:c.1361C>T | NP_004661.2 p.P454L | Missense |
| 17:41246481 T>C (rs1799950) | BRCA1 | NM_007294.3:c.1067A>G | NP_009225.1 p.Q356R | Missense |
| 9:135779052 G>A (rs118203657) | TSC1 | NM_000368.4:c.2194C>T | NP_000359.1 p.H732Y | Missense |
| 1:156212872 T/A (rs1443227492) | BGLAP | NM_199173.3:c.222T>A | NP_954642.1 p.C74X | Stop gain |
| 2:58386928 G/GTAAT | FANCL | NM_018062.3:c.1096_1099dup | NP_060532.2 p.T367Nfs*13 | Frameshift |
| 5:80109533 T/C | MSH3 | NM_002439.2:c.2786T>C | NP_002430.2 p.I929T | Missense |
| 12:124209215 G>T (rs144499089) | ATP6V0A2 | NM_012463.2:c.309G>T | NP_036595.2 p.K103N | Missense |
| 3:51673972 A/T | RAD54L2 | NM_015106.2:c.2188A>T | NP_055921.2 p.I730F | Missense |
| 21:16340242 T/C | NRIP1 | NM_003489.3:c.272A>G | NP_003480.2 p.E91G | Missense |
| 2:149226489 C/T | MBD5 | NM_018328.3:c.977C>T | NP_060798.2 p.A326V | Missense |
| 4:1206089 G/A (rs199614101) | CTBP1 | NM_001328.2:c.1262C>T | NP_001319.1 p.421L | Missense |
| 3:38888684 A/T | SCN11A | NM_014139.2:c.4877T>A | NP_054858.2 p.F1626Y | Missense |
| 1:63876815 A/G | ALG6 | NM_013339.3:c.495-2A>G | Splice acceptor (−2) | Splice acceptor (−2) |
| 1:120056817 T/TGCA | HSD3B1 | NM_000862.2:c.671_672insGCA | NP_000853.1 p.V224_Y225insH | Inframe insertion |
| 4:153332604 TCTC/T | FBXW7 | NM_033632.3:c.349_351del | NP_361014.1 p.E117del | Inframe deletion |
| 6:49700908 G/A | CRISP3 | NM_006061.1:c.521C>T | NP_006052.1 p.A197V | Missense, Splice donor (1) |
| 16:23634293 C>T (rs45551636) | PALB2 | NM_024675.3:c.2993G>A | NP_078951.2 p.G998E | Missense |
| 16:89815152 G>A (rs17233497) | FANCA | NM_000135.2:c.3263C>T | NP_000126.2 p.S1088F | Missense |
| 15:91326099 C>T (rs11852361) | BLM | NM_000057.2:c.2603C>T | NP_000048.1 p.P868L | Missense |
| 18:3452067 G/A (rs202123354) | TGIF1 | NM_170695.2:c.90G>A | NP_733796.2 p.W30X | Stop gain |
| 4:55955969 C/T (rs56302315) | KDR | NM_002253.2:c.3193G>A | NP_002244.1 p.A1065T | Missense, Splice acceptor (1) |
| 17:12901781 A/C (rs149210630) | ELAC2 | NM_018127.5:c.1468T>G | NP_060597.4 p.S490A | Missense |
| 19:50766628 C/T (rs202065396) | MYH14 | NM_001145809.1:c.2645C>T | NP_001139281.1 p.A882V | Missense |
| X:110973633 TGAA/T | ALG13 | NM_001099922.2:c.2383_2385del | NP_001093392.1 p.E795del | Inframe deletion |
| 4:103747794 C/T | UBE2D3 | NM_003340.4:c.-128-1G>A | Splice acceptor (−1) | Splice acceptor (−1) |
| 9:35707745 G/C (rs151033435) | TLN1 | NM_006289.3:c.4615C>G | NP_006280.3 p.L1539V | Missense |
| 1:145578236 C/T (rs142217740) | PIAS3 | NM_006099.3:c.199C>T | NP_006090.2 p.R67W | Missense |
| 10:5014483 T/A (rs146462860) | AKR1C1 | NM_001353.5:c.661T>A | NP_001344.2 p.S221N | Missense |
| 10:5014484 C/A (rs140800505) | AKR1C1 | NM_001353.5:c.662C>A | | Missense |
| 11:47237894,CAGA,C | DDB2 | NM_000107.2:c.139_141del | NP_000098.1 p.R47del | Inframe deletion |
| 17:35564593 G/A (rs144494055) | ACACA | NM_198837.1:c.3544C>T | NP_942134.1 p.R1182W | Missense |
| 7:8633593 A/G | HDAC9 | NM_001204145.1:c.596A>G | NP_009225.1 p.Q356R | Missense |
| 17:41246481 T > C (rs1799950) | BRCA1 | NM_007294.3:c.1067A>G | NP_001191074.1 p.Y199C | Missense |
| 15:43762077 TGGGATA/T | TP53BP1 | NM_001141979.1:c.1362_1367del | NP_002399.1 p.I160S | Inframe deletion |
| 14:50088465 T/G | MGAT2 | NM_002408.3:c.479T>G | NP_009225.1 p.Q356R | Missense |
| 17:41246481 T>C (rs1799950) | BRCA1 | NM_007294.3:c.1067A>G | NP_001135451.1 p.I455_P456del | Missense |
| 2:38298287 T/TGGTGGCATCA (rs72466463) | CYP1B1 | NM_000104.3:c.1200_1209dup | NP_000095.2 p.T404Sfs*30 | Frameshift |
| 10:94297192 C/T | IDE | NM_004969.3:c.214G>A | NP_004960.2 p.G72S | Missense |
| 12:124824917 C/T (rs199692449) | NCOR2 | NM_001077261.3:c.5381G>A | NP_001070729.2 p.R1794Q | Missense |

TABLE 4-continued

Full variant description.

| Variant DNA level | Gene | Variant cDNA level | Variant protein level | Variant class |
|---|---|---|---|---|
| 21:16337279 C/A (rs140803495) | NRIP1 | NM_003489.3:c.3235G>T | NP_003480.2 p.V1079F | Missense |
| 16:23632788 TTTTC/T | PALB2 | NM_024675.3:c.3004_3007del | NP_078951.2 p.E1002Tfs*4 | Frameshift |
| 6:52657698 C/T (rs148795539) | GSTA1 | NM_145740.3:c.502G>A | NP_665683.1 p.E168K | Missense |
| 8:48973252 G/A | UBE2V2 | NM_003350.2:c.302G>A | NP_003341.1 p.R101Q | Missense |
| 20:31021718 C/T (rs373685182) | ASXL1 | NM_015338.4:c.1717C>T | NP_056153.2 p.R573W | Missense, Splice donor (3) |
| 12:53776449 G/C (rs200394677) | SP1 | NM_138473.2:c.718G>C | NP_612482.2 p.G240R | Missense |
| 11:62388048 G>C | B3GAT3 | NM_012200.2:c.178C>G | NP_036332.2 p.R60G | Missense |
| 9:131709581 A/AT | DOLK | NM_014908.3:c.1dup | NP_055723.1 p.M1? | Mutation in start codon |
| 13:28592620 T/C | FLT3 | NM_004119.2:c.2525A>G | NP_004110.1 p.Y842C | Missense |
| 10:94274700 A/G (rs200118524) | IDE | NM_004969.2:c.761T>C | NP_004960.2 p.M254T | Missense |
| 4:70723282 C/G | SULT1E1 | NM_005420.2:c.81G>C | NP_005411.1 p.W27C | Missense |
| 1:120478125 A/C (rs147223770) | NOTCH2 | NM_001200001.1:c.3625T>G | NP_001186930.1 p.F1209V | Missense |
| 17:33430313 T>C (rs28363284) | RAD51D | NM_001142571.1:c.758A>G | NP_001136043.1 p.E223G | Missense |
| 1:182555767 C>T (rs151296858) | RNASEL | NM_021133.3:c.175G>A | NP_066956.1 p.G59S | Missense |

Figure 2B:
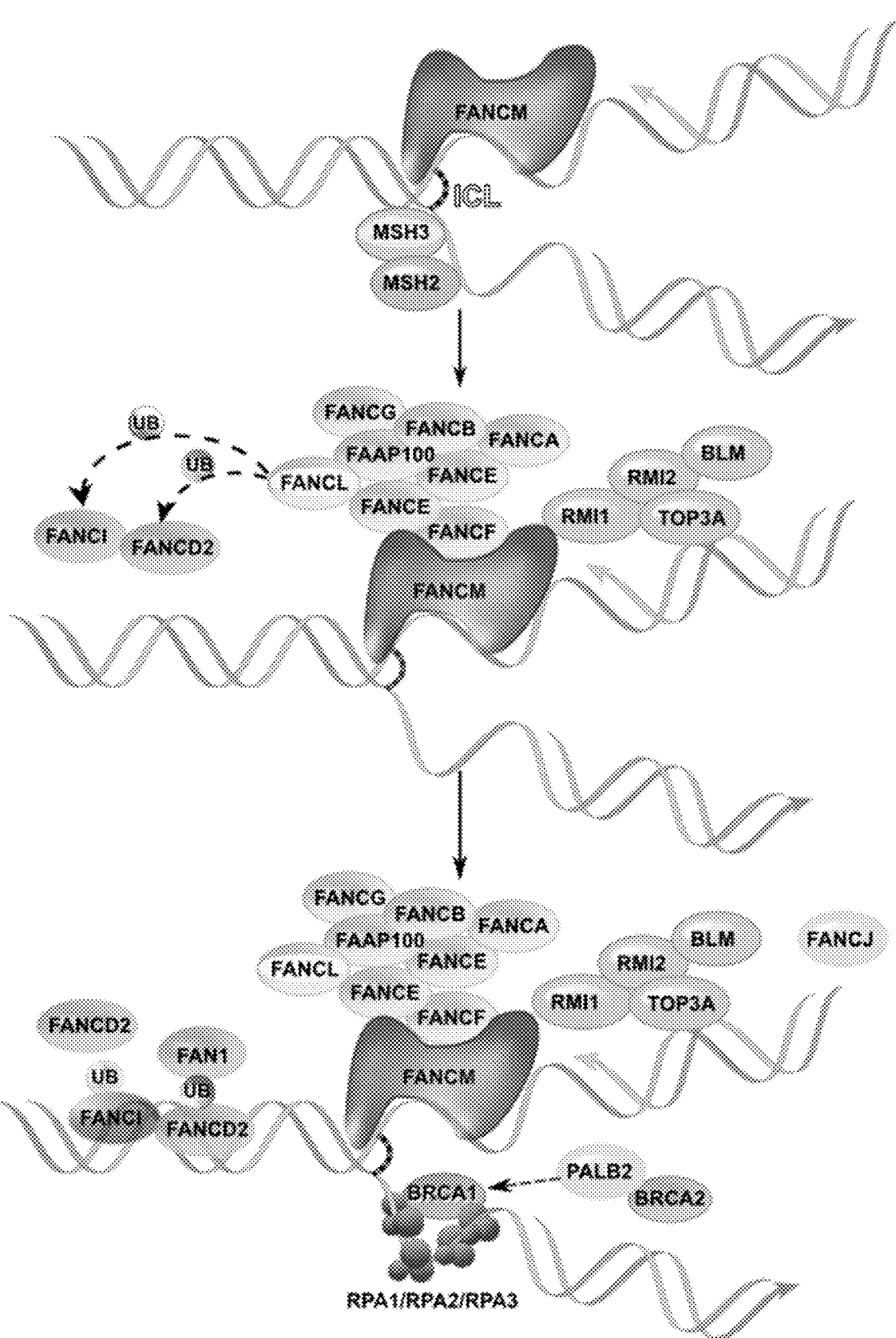
Figure 2C:
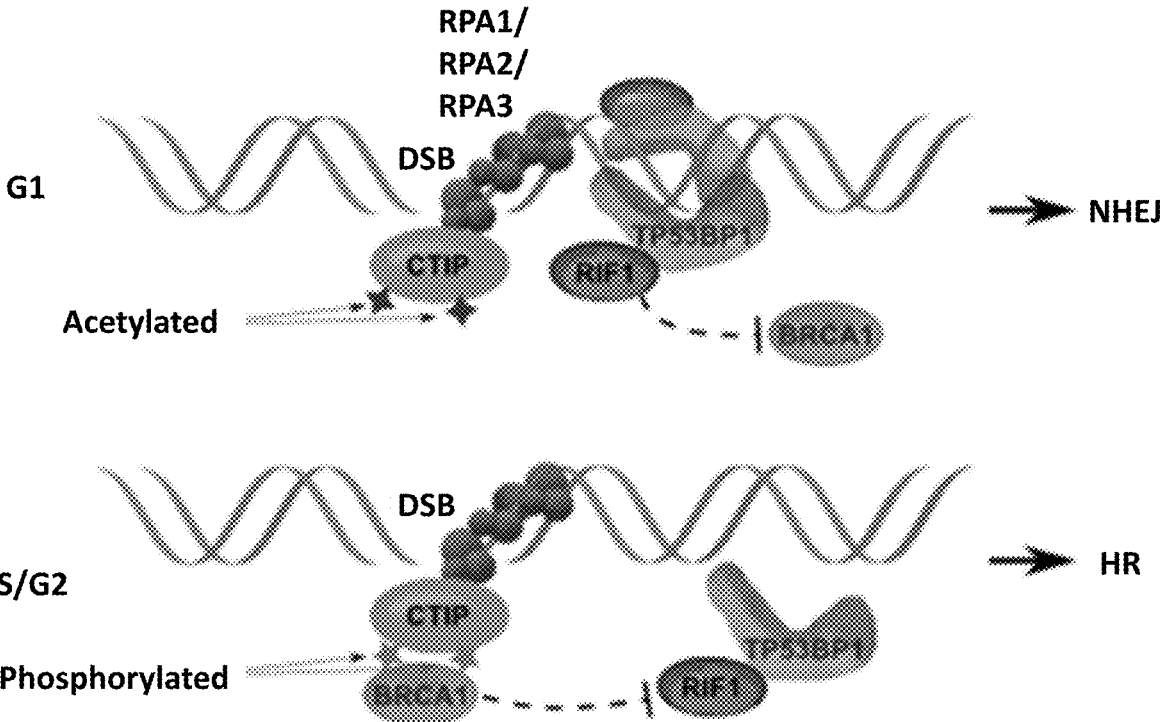

High frequency of variants affecting genes involved in DNA repair and androgen signaling. Nineteen variants affecting the function of genes involved in DNA damage repair (DDR) (with some known to be androgen regulated), and AR-dependent transcription were identified in the patient cohort, with 11/12 patients having at least 1 affected gene in this category, and 5/12 having 2 or more. These genes included PALB2 (also known as FANCN), APTX, BLM, BRCA1, CTBP1, DDB2, FANCA, FANCL, MBD5, MSH3, NEIL3, RAD51D, RAD54L2 (also known as ARIP4), SP1, TP53BP1, UBE2D3, UBE2V2 (also known as MMS2). Many of the proteins encoded by these genes interact to mediate DNA repair functions (FIG. 2B, 2C).

For some patients, a single variant seemed likely to pose substantial risk, such as the frameshift variant E1002Tfs*4 in PALB2 found patient 129748. This patient was diagnosed at age 41, with a father who was also diagnosed prostate cancer at age 67. PALB2 truncating mutations have been detected in patients with Fanconi's anemia and various cancers, including prostate cancer. Importantly, PALB2 p.E1002Tfs*4 lacks part of the WD40 repeat domain (amino acids 853-1186) known to mediate protein interactions with key proteins involved in homologous recombination (HR) such as BRCA2 and RAD51. Potentially magnifying the effect of the PALB2 truncation, this patient also has a mutation (p.R101Q) predicted to damage in the ubiquitin conjugating enzyme UBE2V2, identified as a factor required for avoidance of UV damage, with expression of UBE2V2 linked to prognosis in breast cancers following treatment with DNA damaging therapies.

Some patients had highly suggestive combinations of rare variants. For example, patient 117939 has three independent mutations likely to directly impact DNA damage response: FANCL p.T367Nfs*13, MSH3 p.1929T, and RAD54L2 p.1730F (FIG. 2B). FANCL is an E3 ubiquitin ligase of the Fanconi Anemia (FA) core complex. The mutation T367Nfs*13 produces a protein with premature truncation and three novel amino acids at the C-terminus, and has been described in an FA patient. This mutation produces a hypomorphic mutation with only partial correction of mitomycin C sensitivity and chromosomal defects. MSH3 heterodimerizes with MSH2 to mediate mismatch repair; variants in MSH3 have been associated with risk of some forms of cancer, including prostate.

Crosstalk between FA and MSH2/MSH3 in the mismatch repair pathway has been well documented, with the two operating as redundant DNA damage sensors. RAD54L2/ARIP4 is a DNA helicase that binds the AR, and modulates AR-dependent transactivation in a promoter-dependent manner, and has been linked to a role in DNA repair. 1730 is just downstream of one of the three LXXLL motifs, also known as nuclear boxes, that mediate protein-protein interactions.

In some cases, combinations involving non-rare variants of DDR genes were suggestive. Patient 124604, diagnosed with prostate cancer at age 43, has a pedigree that shows cases of prostate cancer over 3 generations. This patient carries 3 non-rare missense variants in genes involved in DDR: BLM p.P868L, PALB2 p.G998E, and FANCA p.S1088F. BLM encodes a 3'-5' DNA helicase which functions in maintenance of genomic stability, with inactivating mutations associated with a progeria, Bloom Syndrome (BS). BLM p.P868L has been characterized as an allele that is unlikely to cause BS, but causes partial loss of function manifested by an intermediate sensitivity to hydroxyurea, and has been associated with increased rectal cancer risk. Interestingly, an uncle of patient 124604 had colorectal cancer. The PALB2 p.G998E variant in this patient was reported at a similar frequency of ~10% in a population of BRCA1- and BRCA2-negative male breast cancer patients in Northern Italy as was observed in healthy individuals. A similar high rate of occurrence in normal populations was observed for FANCA p.S1088F (9/97 in breast cancer cases vs 11/94 in controls). However, the assortment of three independent alleles affecting DNA repair in the pedigree of this patient may well have an additive effect, given the involvement of all three proteins in related DNA repair pathways (FIG. 2B).

In a similar case, Patient 112940 had a rare variant causing a stop at amino acid 56, eliminating function of APTX (aprataxin), involved in the repair of multiple forms of DNA breaks and implicated in therapeutic response in cancer, and a second rare variant (p.F460C) damaging NEIL3, a DNA glycosylase involved in the base excision repair pathways that protects cells from genotoxic stress and has been associated with prostate cancer risk. This patient, as well as 3 other unrelated individuals (Patients 117197, 126002, and 129413), all had the same non-rare variant in BRCA1, p.Q356R, which some prior studies have linked to prostate cancer risk; an observed incidence of 33%, versus the expected incidence of this variant should be 9%, based on ExAC. Like patient 112940, the other patients also possessed multiple additional candidate rare variants affecting DNA damage response and/or genes related to androgen function.

Patient 129413 had a mutation disrupting TP53BP1 (p.I455_P456del, predicted to be deleterious by PROVEAN), TP53BP1 competes with BRCA1 for directing proteins down the non-homologous end joining (NHEJ) versus homologous recombination (HR) repair pathway (FIG. 2C); in the context of impaired TP53BP1, or other DDR defects, and as discussed further below, the BRCA1 variant may have more deleterious effect.

Figure 3A:
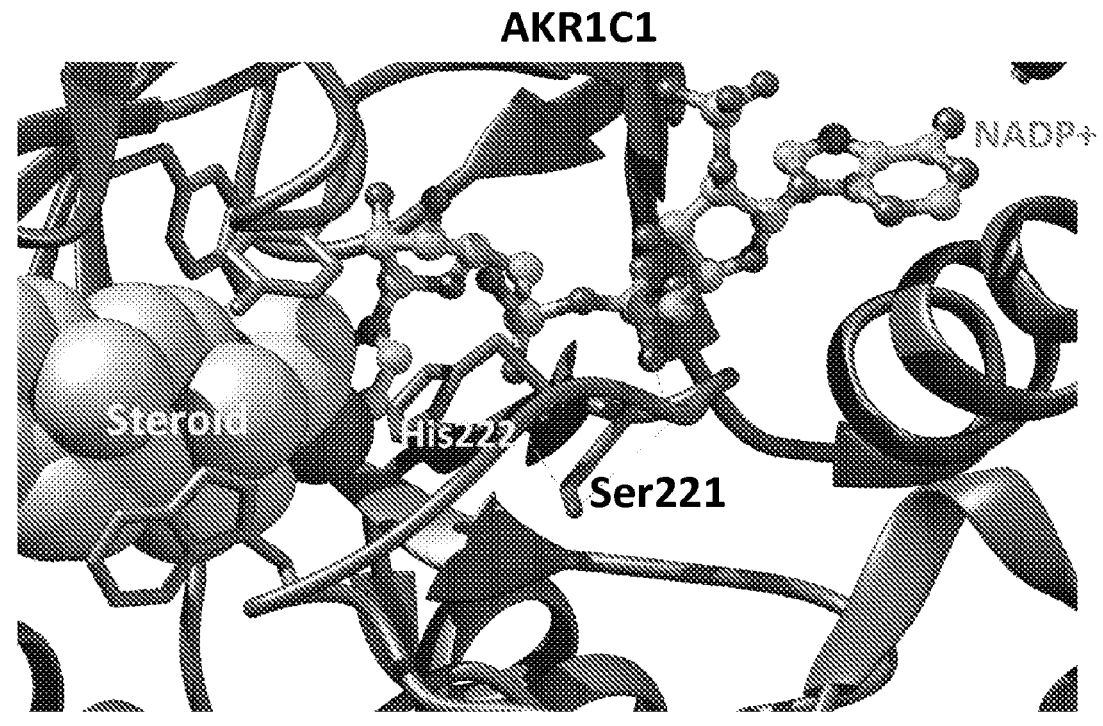
FIGS. 3A and 3B show functional defects associated with novel missense variants.

In some cases, patients have mutational profiles in which disruption of DDR and AR signaling is closely linked. For example, patient 125671 has an in-frame deletion (p.R47del) in the AR-interacting protein DDB2: the R47 residue mediates high affinity binding of DDB2 to damaged DNA. This patient also has an S221N variant predicted to be highly deleterious (FIG. 3A) in AKR1C1, a member of an enzyme family that controls concentrations of active androgens and other steroidal hormones, regulates trans-activation of AR in the prostate, and has been shown to regulate resistance to the anti-androgen enzalutamide, recently approved for treatment of castration resistant prostate cancer.

Patient 123136 comes from a family with a high burden of cancer, with a sister affected with melanoma and breast cancer, father with lung cancer, and mother with colon cancer. This patient has a rare variant (p.P421L) of CtBP1, a coregulator of BRCA1, that has been linked to risk of prostate cancer. Activation of the AR regulator HIPK2 (Homeodomain-Interacting Protein Kinase 2) by genotoxic stress triggers apoptosis in part through phosphorylation of CtBP1, which causes CtBP1 degradation; loss of this signaling could plausibly cause predisposition to multiple forms of cancer. P421L destroys the HIPK2 phosphorylation site on CtBP1.

Other classes of variants. In addition to the selected examples described above, rare variants were identified in all of the categories from the candidate list. Variants relating to androgen availability and AR-dependent transcription were identified. Without intending to be limited to any particular theory or mechanism of action, it is believed that these variant combinations may suggest a possible explanation for why mutations in the DDR machinery, which theoretically could increase risk of any type of cancer, results in a familial predilection for prostate cancer.

As selected examples, two patients, 129547 and 117939, had disruptive mutations in NRIP1 (also known as RIP140), a co-receptor for estrogen, androgen, and other classes of nuclear hormone receptor. Disruption of NRIP1 function has been reported to lead to hyperactivation of AR signaling, and variants in NRIP1 have been linked to risk in breast, endometrial, and other cancers. Interestingly, patient 129547 also has a rare variant affecting a second AR co-repressor, NCOR2 (also known as SMRT) that limits AR signaling, while patient 117939 has a rare variant in an alternative AR cofactor, RAD54L2 (also known as androgen receptor interacting protein 4, ARIP4). These variant pairs may interact to de-repress AR signaling in these two patients.

Another patient, 117197, has a frameshift variant (Q1340Rfs*43) in EFCAB6 (also known as DJBP), which encodes a protein that recruits histone-deacetylase (HDAC) complexes to repress AR-dependent transcription; the variant eliminates the HDAC-interaction domain. Patient 124604, noted above as having 3 variants in DDR-related proteins (BLM, PALB2, and FANCA), has a family with prostate cancer over 3 generations. This patient also has a splice site-disrupting variant in CRISP3 (cysteine-rich secretory protein 3). Expression of CRISP3 is prostate-specific, and CRISP3 up-regulated in a subset of prostate cancers, especially prostate cancer with the TMPRSS2-ERG fusion gene. Mis-splicing due to the G/A mutation in 6:49700908 would destroy the CRISP domain (pfam: 08562), which allows CRISP3 to regulate ryanodine receptor Ca2+ signaling. ExAC data indicates the position is multi-allelic with another allele (T) mainly represented in African populations.

Figure 3B:
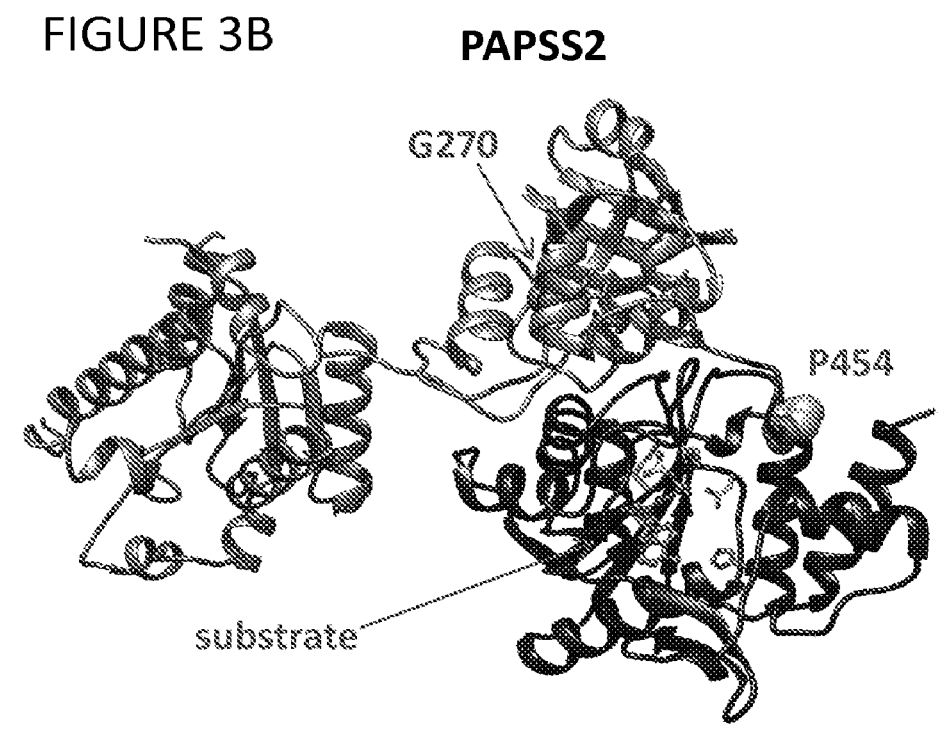

A major function of the prostate is in production of glycoproteins, including PSA, that support sperm production, and changes in glycosylation are associated with prostatic neoplasms and response to androgen treatment. Among a number of variants in genes linked to glycosylation defects (PAPSS2, ATP6V0A2, ALG13, MGAT2, B3GAT3, DOLK), the variant in PAPSS2 seems the most interesting. This variant (p.P454L; FIG. 3B) is strongly predicted to destroy the catalytic function of PAPSS2, a kinase and ATP sulfurylase that catalyzes two sequential reactions to synthesize PAPS, the sulfate source for sulfation of the androgen precursor didehydroepiandrosterone (DHEA). Of particular relevance to prostate cancer, two mutations in PAPSS2 have been reported as causing androgen excess via complete (W362Cfs*3) or partial (G270D) disruption of DHEA sulfation.

Finally, patients also had damaging variants in genes linked to inherited or somatic forms of other cancers, although not well validated for prostate, including FLT3, ASXL1, KDR, NOTCH2; or genes which are identified by the candidate criteria noted above (Table 2), but for which limited information is available based on functional characterization to date (e.g., IDE interacts directly with AR, but the impact of the association is unclear). The p.Y842C mutation found in patient 131534 affects the highly conserved activation loop of FLT3, a kinase frequently activated in patients with acute myeloid leukemia (AML). Transfection of FLT3 p.Y842C in 32D cells showed constitutive FLT3 tyrosine phosphorylation and interleukin 3 (IL-3)-independent growth, and activating mutations in FLT3 have been shown to increase DNA damage as a consequence of elevated production of increased reactive oxygen species (ROS). Mutational activation of the KDR (also known as VEGFR2) kinase is common in angiosarcomas and seen in many other tumors; the KDR p.A1065T variant found in patient 124853 is constitutively active.

Figure 4A:
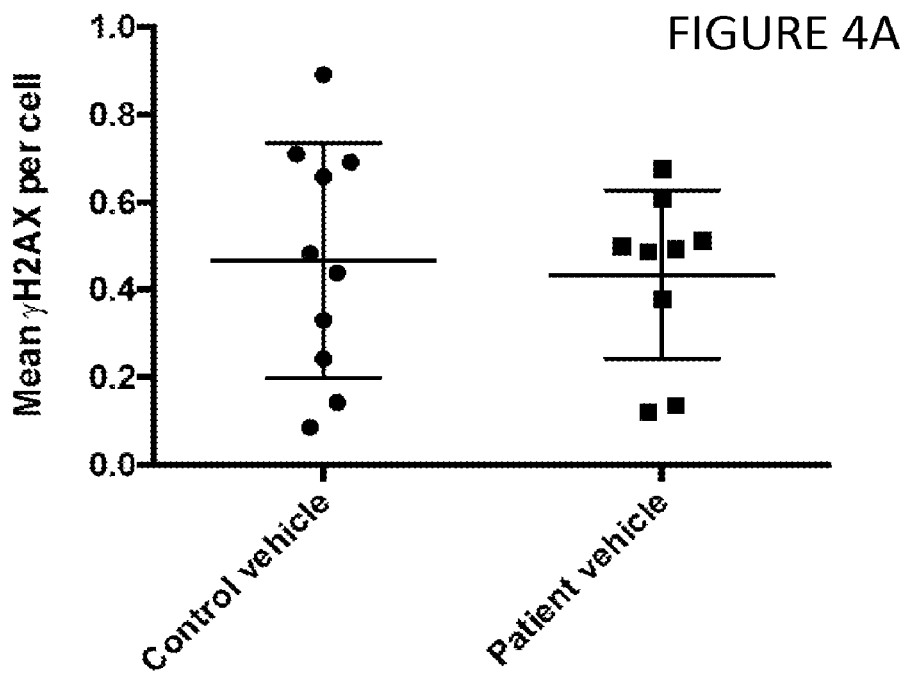
FIGS. 4A-4C show elevated γH2AX in T-cells from patients with prostate cancer following treatment with DNA damaging agents. Primary T-cells from 9 patients and 10 age- and sex-matched controls were stimulated by PHA and IL-2, then treated with vehicle, aphidicolin or etoposide, and stained for nuclear γH2AX foci.
Figure 4B:
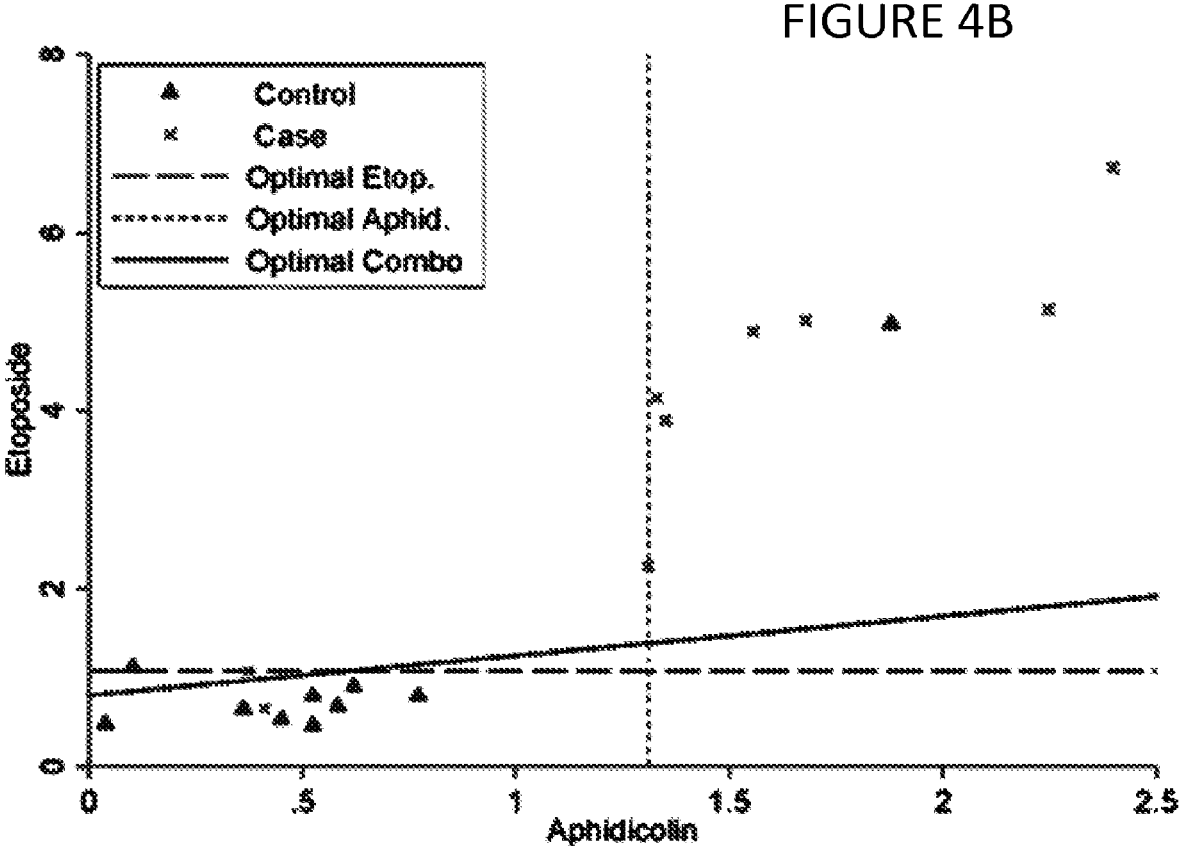
Figure 4C:
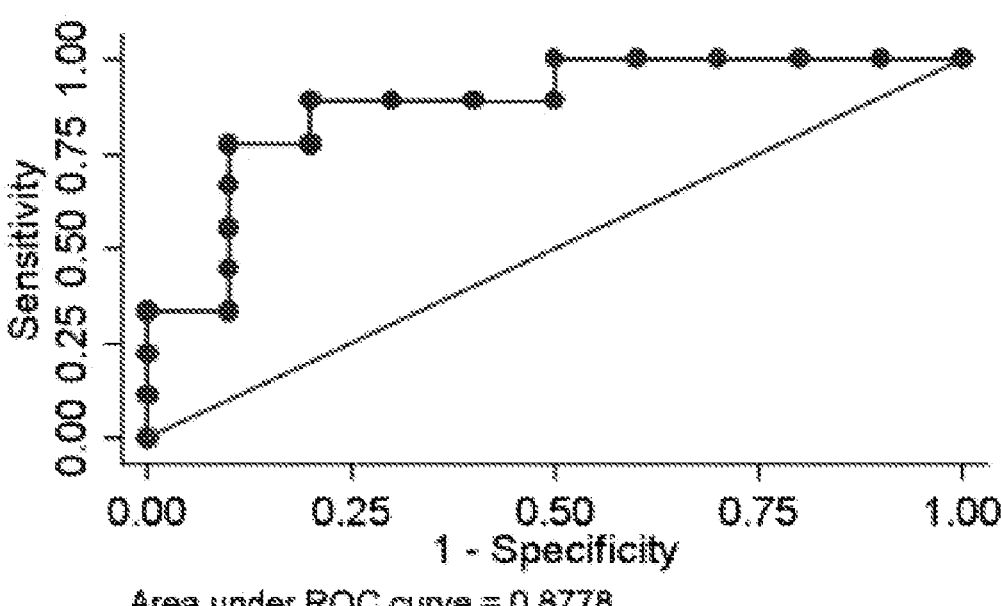

Functional defects in response to DNA damaging agents in the lymphocytes of patients of prostate cancer patients with familial risk. Given the strong implication of defects in genes involved in DNA repair as causative factors for numerous classes of hereditary cancer, these genes were of particular interest. PBLs were available for 9/12 patients, allowing the assessment of whether the response of these cells to low doses of DNA damaging agents differed from those of 10 age and gender-matched individuals without a cancer diagnosis or a family history of cancer. Immunofluorescence was used to assay the formation of DSB-associated γ (phospho)-H2AX foci in cells with and without treatment with the DNA polymerase inhibitor aphidicolin or the topoisomerase II inhibitor etoposide. Under baseline conditions without drug treatment, the patient and control groups were statistically indistinguishable (p=0.746) (FIG. 4A). However, treatment of cells with low doses of aphidicolin (p=0.0337) or etoposide (p=0.007) revealed significant differences in γH2AX induction between cases and controls, with a higher magnitude of induction seen in prostate cancer patients (FIG. 4B). Receiver operating characteristic (ROC) curve analysis for the combination of both treatments indicated specificity and selectivity of observed differences were 87% (FIG. 4C).

EXAMPLE 3

Summary

With the growing availability of powerful technologies for genomic analysis, risk assessment is reaching an inflection point. In this disclosure, efforts were focused on the analysis of defects in DDR in individuals with family risk factors for prostate cancer. This approach identified variants or variant combinations in almost every patient assessed that have the potential to alter response to DNA damage, with findings further supported by direct demonstration of elevated expression of γH2AX following administration of DNA damaging stimuli. In the group of patients examined, variants often occurred in combinations that would be predicted to interact to weaken DDR and, typically, each variant was idiopathic to the individuals investigated.

The disclosure also identified non-rare variants affecting DDR. For example, in the cohort analyzed here, 33% of patients had the same non-rare p.Q356R variant in BRCA1, instead of the expected 9%. BRCA1 p.Q356R is a rare example of a variant that has a frequency of minor allele over 5% and an increased odds ratio for breast cancer over 1.5 in carriers. In a prior study on association between prostate cancer risk and SNPs in a 200-kb area around the BRCA1 gene, the strongest link was for BRCA1 p.Q356R, with the R allele preferentially transmitted to men affected with prostate cancer before the age of 50. Q356 is located in the MRE11/RAD50/NBS1 (MRN) domain, required for interaction with RAD51, p53, ZBRK1, SWI/SNF, BRAP2, ATPase, and Importin α.

ZBRK1/ZNF350 interactions with CtIP and BRCA1 mediates BRCA1-dependent transcriptional repression of target genes: Q356R disrupts the interaction between BRCA1 and ZBRK1, eliminating the transcriptional co-repressor function of BRCA1, and upregulation of such BRCA1-CtIP-ZBRK1 target genes as angiopoietin-1 (ANG1), which promotes angiogenesis and proliferative cell potential. In a prior study of 931 prostate cancer patients, 13 independent variants of uncertain significance were identified in the MRE11/RAD50/NBS1 domain including Q356R. The data from this disclosure reinforce the idea that this variant may be significant in the context of other variants that weaken DDR.

The candidate approach also considered variants predicted to influence signaling by androgens and other hormones, or prostate-specific functions such as control of glycosylation. For a number of the patients, damaging rare variants were also found in genes with these properties and, without intending to be limited to any particular theory or mechanism of action, it is believed that this may impact the manifestation of a defect in a DDR gene as initiation and progression of a tumor of the prostate, rather than of another tissue. Under this interpretation, it is believed that the high incidence of multiple forms of cancer in the families of a number of the individuals assessed may reflect the assortment of variants affecting DDR from those involved with organ-specific functions.

Of particular relevance to prostate cancer, the androgen receptor has been found to regulate a suite of DDR genes, including some that promote resistance to radiotherapy in prostate cancer in part by promotion of non-homologous end joining (NHEJ) repair. This disclosure provides data on specific pathways analysis of exomes of a group of case-only prostate cancer patients who underwent clinical genetic evaluation for inherited cancer risk based on personal and/or family cancer features. Predisposing variants were identified in every case, with a particular bias towards evidence of DDR-impairing defects in most cases. Based on this work, functional testing demonstrated increased sensitivity to DNA damaging agents for lymphocytes from prostate cancer patients bearing predicted DNA damaging alleles.

In this disclosure, the functional testing of patient-derived peripheral blood lymphocytes (PBLs) has supported the idea that responses to DNA damage in prostate cancer patients differ from those found in age and gender-matched controls. This approach can potentially be extended using systematic cell-based functional assays for phenotyping of missense alleles.

Another potentially valuable aspect of such broader testing may be implications for patient treatment. The variability in the aggressiveness of the newly diagnosed cases makes it challenging for the clinician to identify appropriate males to treat, and identifying the correct treatment approach. Modalities for treatment include and are not limited to active surveillance, radical prostatectomy (RP), radiation and other DNA-damaging therapies, and androgen deprivation therapy (ADT). Identifying a variant that renders the cell dependent on a specific pathway may create an opportunity for synthetic lethality, as in the example of BRCA mutations and PARP inhibitors. Conversely, identifying underlying defects in androgen signaling may be useful in stratifying response to ADT. At present, both the risk of and the choice between treatment options for prostate cancer pose considerable psychological stress to patients.

The invention is not limited to the embodiments described and exemplified above, but is capable of variation and modification within the scope of the appended claims.

SEQUENCE LISTING

The patent contains a lengthy sequence listing. A copy of the sequence listing is available in electronic form from the USPTO web site (https://seqdata.uspto.gov/docdetail?docId=US12674206B2). An electronic copy of the sequence listing will also be available from the USPTO upon request and payment of the fee set forth in 37 CFR 1.19(b)(3).

We claim:

1. A method for reducing the risk of developing prostate cancer in a human subject comprising:

(a) isolating peripheral blood lymphocytes from the human subject and treating at least a portion of the isolated peripheral blood lymphocytes with a low dose of an agent or radiation that induces double stranded breaks in DNA;

(b) quantifying a level of gamma-H2AX foci in the peripheral blood lymphocytes treated with the low dose of the agent or radiation;

(c) assaying nucleic acid molecules from the peripheral blood lymphocytes of (b) for the presence or absence of one or more altered genes, the one or more altered genes:

(i) comprising an ALG6 gene having an alteration in a splice site acceptor sequence; or (ii) encoding one or more variant proteins selected from the group consisting of aprataxin (APTX) R56X, breast cancer 1 (BRCAI) Q356R, nei-like DNA glycosylase 3 (NEIL3) F460C, EF-Hand Calcium Binding Domain 6 (EFCAB6) Q1340Rfs*43, Cytochrome P450 Family 1 Subfamily B Member 1 (CYP1B 1) D218V, CYP1B1 T404Sfs*30, 3'-Phosphoadenosine 5'-Phosphosulfate Synthase 2 (PAPSS2) P454L, TSC Complex Subunit 1 (TSC1) H732Y, Bone Gamma-Carboxyglutamate Protein (BGLAP) C74X, Fanconi Anemia complementation group L (FANCL) T367Nfs*13, mutS homolog 3 (MSH3) I929T, ATPase H+ Transporting V0 Subunit A2 (ATP6VOA2) K103N, helicase ARIP4/androgen receptor-interacting protein 4 (RAD54L2) I730F, Nuclear Receptor Interacting Protein 1 (NRIP1) E91G, NRIP1 V1079F, methyl-CpG-binding domain protein 5 (MBD5) A326V, C-terminal binding protein 1 (CTBP1) P421L, Sodium Voltage-Gated Channel Alpha Subunit 11 (SCN11A) F1626Y, Hydroxy-Delta-5-Steroid Dehydrogenase (HSD3B1) V224-Y225insH, F-Box And WD Repeat Domain Containing 7 (FBXW7) E117del, partner and localizer of BRCA2 (PALB2) E1002Tfs*4, PALB2 G998E, Fanconi Anemia complementation group A (FANCA) S1088F, Bloom Syndrome RecQ Like Helicase (BLM) P868L, Cysteine Rich Secretory Protein 3 (CRISP3) A197V, TGFB Induced Factor Homeobox 1 (TGIF1) W30X, Kinase Insert Domain Receptor (KDR) p.A1065T, ElaC Ribonuclease Z 2 (ELAC2) S490A, Myosin Heavy Chain 14 (MYH14) A882V, Acetylglucosaminyltransferase (ALG13), E795del, ubiquitin-conjugating enzyme E2 D3 (UBE2D3), Talin 1 (TLN1) L1539V, Protein Inhibitor Of Activated STAT 3 (PIAS3) R67W, aldo-keto reductase family 1, member C1 (AKR1C1) S221N, damage-specific DNA binding protein 2 (DDB2) R47del, Acetyl-CoA Carboxylase Alpha (ACACA) R1182W, Histone Deacetylase 9 (HDAC9) Y199C, Mannoside Acetylglucosaminyltransferase 2 (MGAT2) 1160S, tumor suppressor p53 binding protein 1 (TP53BP1) I455-P456del, Insulin Degrading Enzyme (IDE) G72S, IDE M254T, Nuclear Receptor Corepressor 2 (NCOR2) R1794Q, Glutathione S-Transferase Alpha 1 (GSTA1) E168K, ubiquitin-conjugating enzyme E2 V2 (UBE2V2) R101Q, Additional Sex Combs Like 1 (ASXL1) R573W, Sp1 transcription factor (SP1) G240R, Beta-1,3-Glucuronyltransferase 3 (B3GAT3) R60G, Dolichol Kinase (DOLK) MINfs, Fms-Like Tyrosine Kinase 3 (FLT3) Y842C, Sulfotransferase 1E1 (SULTIE1) W27C, NOTCH2 F1209V, RAD51 paralog D (RAD51D) E223G and Ribonuclease L (RNA-SEL) G59S;

(d) determining that the human subject is predisposed to developing prostate cancer based on:

(i) the quantified level of gamma-H2AX foci in the peripheral blood lymphocytes of step (b) being at least 50% higher than a reference number of gamma-H2AX foci obtained using lymphocytes from a healthy individual; and (ii) the assaying step of (c) identifying the presence of the one or more altered genes; and (e) treating the human subject determined to be predisposed to developing prostate cancer according to step (d) with a treatment regimen comprising:

(i) prostatectomy, androgen deprivation therapy, a PARP inhibitor, or one or more of diet management, vitamin supplementation, nutritional supplementation, exercise, psychological counseling, social counseling, education, and regimen compliance management; and, (ii) an enhanced regimen for monitoring prostate cancer development, wherein the enhanced regimen is more frequent or more aggressive than monitoring provided to average-risk individuals;

wherein the human subject is the subject identified as predisposed in step (d).

2. The method of claim 1, wherein the agent that induces double stranded breaks in DNA comprises aphidicolin or etoposide.

3. The method of claim 1, wherein the one or more altered genes comprise rare variants.

4. The method of claim 3, wherein the rare variants comprise rare single nucleotide variants.

5. The method of claim 1, wherein the one or more altered genes comprise a combination of rare variants and non-rare variants.

6. The method of claim 5, wherein the rare variants comprise rare single nucleotide variants.

7. The method of claim 1, wherein the one or more altered genes encode a stop codon that results in a truncated protein with no functionality following expression of the protein.

8. The method of claim 1, wherein the one or more altered genes encode one or more variant proteins selected from the group consisting of aldo-keto reductase family 1, member C1 (AKR1C1) S221N, partner and localizer of BRCA2 (PALB2) E1002Tfs*4, PALB2 G998E, aprataxin (APTX) R56X, bloom syndrome RecQ Like Helicase (BLM) P868L, breast cancer 1 (BRCA1) Q356R, C-terminal binding protein 1 (CTBP1) P421L, damage-specific DNA binding protein 2 (DDB2) R47del, Fanconi Anemia complementation group A (FANCA) S1088F, Fanconi Anemia complementation group L (FANCL) T367Nfs*13, methyl-CpG-binding domain protein 5 (MBD5) A326V, mutS homolog 3 (MSH3) I929T, nei-like DNA glycosylase 3 (NEIL3) F460C, RAD51 paralog D (RAD51D) E223G, helicase ARIP4/androgen receptor-interacting protein 4 (RAD54L2) I73OF, Sp1 transcription factor (SP1) G240R, tumor suppressor p53 binding protein 1 (TP53BP1) 1455-P456del, ubiquitin-conjugating enzyme E2 D3 (UBE2D3), and ubiquitin-conjugating enzyme E2 V2 (UBE2V2) R101Q.

9. The method of claim 8, wherein the one or more altered genes encode a protein comprising PALB2 E1002Tfs*4 or PALB2 G998E.

10. The method of claim 8, wherein the one or more altered genes encode a protein comprising FANCL T367Nfs*13, MSH3 I929T, or RAD54L2 I730F.

11. The method of claim 8, wherein the one or more altered genes encode a protein comprising BLM P868L, PALB2 E1002Tfs*4, PALB2 G998E, or FANCA S1088F.

12. The method of claim 8, wherein the one or more altered genes encode a protein comprising APTX R56X or NEIL3 F460C.

13. The method of claim 8, wherein the one or more altered genes encode a protein comprising APTX R56X, NEIL3 F460C, or BRCA1 Q356R.

14. The method of claim 8, wherein the one or more altered genes encode a protein comprising TP53BP1 1455-P456del.

15. The method of claim 8, wherein the one or more altered genes encode a protein comprising TP53BP1 1455-P456del or BRCA1 Q356R.

16. The method of claim 8, wherein the one or more altered genes encode a protein comprising DDB2 R47del.

17. The method of claim 8, wherein the one or more altered genes encode a protein comprising CTBP1 P421L.

18. The method of claim 8, wherein the one or more altered genes encode a protein comprising AKR1C1 S221N.

19. The method of claim 1, wherein the one or more altered genes encode a protein comprising NRIP1 E91G, NRIP1 V1079F, EFCAB6 Q1340Rfs*43, or CRISP3 A197V.

20. The method of claim 1, wherein the one or more altered genes encode a protein comprising PAPSS2 P454L, ATP6VOA2 K103N, ALG13 E795del, MGAT2 I160S, B3GAT3 R60G, DOLK MINfs, FLT3 Y842C, ASXL1 R573W, KDR pA1065T, or NOTCH2 F1209V.

21. The method of claim 20, wherein the one or more altered genes encode a protein comprising PAPSS2 P454L.

22. The method of claim 20, wherein the one or more altered genes encode a protein comprising FLT3 Y842C, ASXL1 R573W, KDR p.A1065T, or NOTCH2 F1209V.

* * * * *